United States Patent
Shellenberger et al.

(10) Patent No.: US 11,129,918 B1
(45) Date of Patent: Sep. 28, 2021

(54) AIR SANITATION DEVICES AND SYSTEMS

(71) Applicant: Rheem Manufacturing Company, Atlanta, GA (US)

(72) Inventors: Timothy J. Shellenberger, Tyrone, GA (US); Troy E. Trant, Montgomery, AL (US); Atilhan Manay, Roswell, GA (US); Shubham Srivastava, Montgomery, AL (US)

(73) Assignee: Rheem Manufacturing Company, Atlanta, GA (US)

( * ) Notice: Subject to any disclaimer, the term of this patent is extended or adjusted under 35 U.S.C. 154(b) by 0 days.

(21) Appl. No.: 17/064,875

(22) Filed: Oct. 7, 2020

Related U.S. Application Data

(60) Provisional application No. 63/058,669, filed on Jul. 30, 2020.

(51) Int. Cl.
    *A61L 9/20* (2006.01)
(52) U.S. Cl.
    CPC ............ *A61L 9/20* (2013.01); *A61L 2209/111* (2013.01); *A61L 2209/12* (2013.01)
(58) Field of Classification Search
    CPC ...... A61L 9/20; A61L 9/205; A61L 2209/111; A61L 2209/12; A61L 2209/15; A61L 2209/16
    See application file for complete search history.

(56) References Cited

U.S. PATENT DOCUMENTS

| | | | | |
|---|---|---|---|---|
| 3,518,046 A | * | 6/1970 | Cicirello | A61L 9/20 96/224 |
| 5,225,167 A | * | 7/1993 | Wetzel | F24F 3/16 96/224 |
| 5,616,172 A | * | 4/1997 | Tuckerman | F24F 3/1603 96/16 |
| 6,680,028 B1 | * | 1/2004 | Harris | B03C 3/32 422/122 |

FOREIGN PATENT DOCUMENTS

| | | |
|---|---|---|
| EP | 2529759 A1 | 12/2012 |
| WO | 2005039659 A1 | 5/2005 |

OTHER PUBLICATIONS

Kowalski et al., Airborne respiratory diseases and mechanical systems for control of microbes, HPAC Heating/Piping/Air Conditioning, Jul. 1998, pp. 34-48.

(Continued)

*Primary Examiner* — Timothy C Cleveland
(74) *Attorney, Agent, or Firm* — Troutman Pepper Hamilton Sanders LLP; James E. Schutz; Micah B. Hensley

(57) ABSTRACT

An air sanitation device is disclosed. The air sanitation device can include a base section, a body section, and an air movement device configured to move air through at least a portion of the air sanitation device. The air sanitation device can move air from an inlet of the air sanitation device, and past an ultraviolet (UV) light source, and out an outlet of the air sanitation device. The air sanitation device can be configured to draw in air from within or below a breathing (Continued)

zone. The air sanitation device can be configured to draw in air from below the breathing zone and output sanitized air. The sanitized air can be outputted at an angle such that the sanitized air flows in a generally downward direction.

19 Claims, 16 Drawing Sheets

(56) References Cited

OTHER PUBLICATIONS

Yu et al., Ventilation of general hospital wards for mitigating infection risks of three kinds of viruses including Middle East respiratory syndrome coronavirus, Indoor and Built Environment, 2017, vol. 26(4), pp. 514-527.
Gupta et al., Characterizing exhaled airflow from breathing and talking, Indoor Air, 20, pp. 31-39.
Memarzadeh et al., Role of air changes per hour (ACH) in possible transmission or airborne infections, Building Simulation, 2012, vol. 5, pp. 15-28.

* cited by examiner

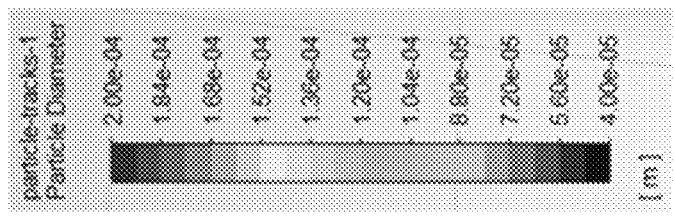
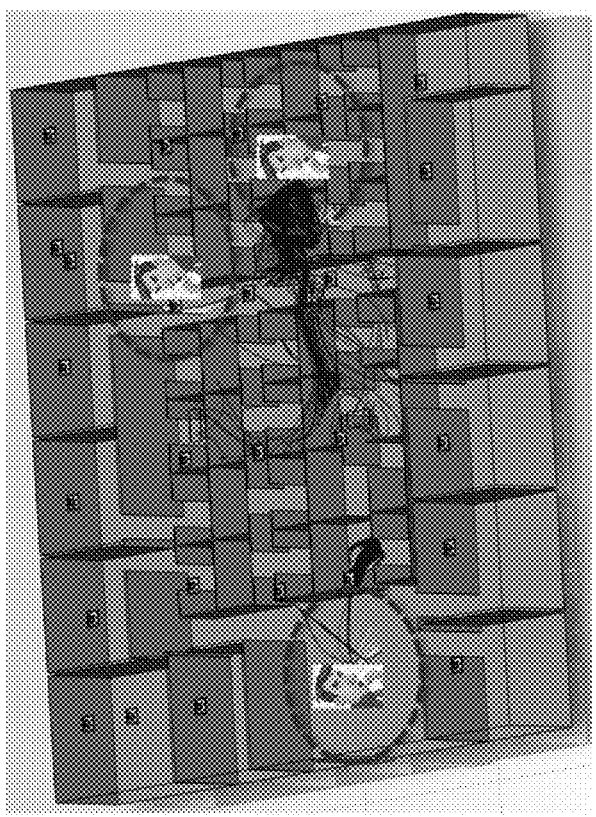
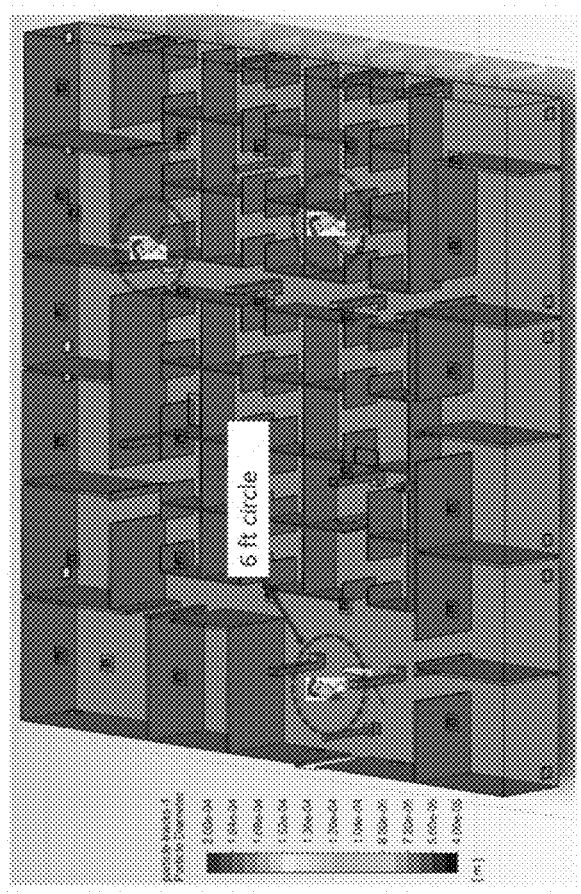
FIG. 6A
FIG. 6B

AIR SANITATION DEVICES AND SYSTEMS

CROSS-REFERENCE TO RELATED APPLICATIONS

This application claims the benefit, under 35 U.S.C. § 119, of U.S. Provisional Patent Application No. 63/058,669, filed 30 Jul. 2020, the entire contents and substance of which is incorporated herein by reference in its entirety as if fully set forth below.

BACKGROUND

The COVID-19 pandemic has disrupted countless people's lives, and efforts to prevent or slow spread of the disease has forced a large number of businesses, schools, and facilities, and events to close or severely reduce the number of people permitted in a single location. Research cited by Centers for Disease Control and Prevention (CDC) and World Health Organization (WHO) suggests there is strong evidence that the disease is commonly transmitted via airborne microdroplets emanating from a person's mouth. These microdroplets can exit a person's mouth while that person is sneezing, talking, or even simply breathing.

To help prevent or slow the spread of COVID-19, certain guidelines have been issued to the public. For example, the CDC has provided guidelines to the public, which includes the instruction to wear a mask or face covering. However, some may find a mask to be uncomfortable, cumbersome, or too restrictive to wear for long durations. Another CDC guidelines instructs the public to practice social distancing, where a person maintains a distance of at least six feet away from other people not from the person's household. However, various scenarios tested with computational fluid dynamics (CFD) simulations indicate that the six-foot social distancing guideline is insufficient in an indoor environment, especially if the heating, ventilation, and air conditioning (HVAC) system that services the indoor environment has not been modified and/or outfitted to prevent the routing of microdroplets into the breathing zone. As will be appreciated, the breathing zone can correspond to the volume within an indoor environment that exists in the range from approximately 4.5 feet (approximately 1.4 meters) from the floor to approximately 7.2 feet (approximately 2.2 meters) from the floor. Illustrations of the results of CFD simulations relating to persons' sneezing in a typical indoor environment are shown in FIGS. 6A and 7A, with FIG. 6A depicting lateral movement of microdroplets created by the sneezes and FIG. 7A depicting vertical movement of microdroplets created by the sneezes. As can be seen, the microdroplets tend to travel within the breathing zone and well outside of the six-foot social distancing guideline.

Such problem can become more pronounced with HVAC systems that have an overhead ventilation configuration in which both the supply vents and the return vents are located overhead. This can result in circulation of air within the conditioned space, which promote high circulation of microdroplets, which can carry COVID-19. Other HVAC system configurations, such as downflow ventilation systems (e.g., overhead supply vents and floor-level return vents), can provide a decreased amount of circulation within the conditioned space as compared to overhead ventilation systems, but even these HVAC systems can promote an undesirably high amount of air circulation within the conditioned space, which can facilitate movement of microdroplets within the conditioned space. This can increase the chances that a person will inhale or ingest the microdroplets, which can facilitate transmission of COVID-19 or other airborne pathogens. As will be appreciated, the increased air circulation within a conditioned space can undercut the effectiveness of social distancing such that other preventive measures are necessary while indoors.

To that end, some HVAC systems have been modified to include filters and/or sanitizing devices, such as ultraviolet (UV) light sources, which can help sanitize the air within a conditioned space. HVAC systems including UV light sources are typically configured to expose the air within a duct of the HVAC system to UV radiation. Such preventive measures can sanitize the air that exits from the supply vents into the conditioned space. However, such preventive measures are of no help in ensuring sanitization of air within the space itself (i.e., air that has exited a supply vent but has not yet entered a return vent). Thus, even with existing preventive measures in place, there can still be a high likelihood that microdroplets containing COVID-19 or another pathogen are being circulated within the conditioned space.

Accordingly, there is a need for devices, systems, or other preventive measures that can help prevent the transmission of microdroplets from person to person, particularly within indoor spaces. It is desirable for such devices, systems, or other preventive measures to require no action on the part of an individual.

SUMMARY

These and other problems are addressed by the technologies described herein. The disclosed technology relates generally to devices and systems configured to remove and/or divert microdroplets and/or aerosols, which can carry COVID-19 or other pathogens, from the face of some or all of persons located within a room or other space. However, the disclosed technology is not so limited. For example, the disclosed technology includes devices and systems configured to sanitize air flowing within a space.

The disclosed technology includes an air sanitation device the includes a base section and a body section. The base section can include one or more inlets disposed at a height that is less than or equal to approximately 4.5 feet with respect to a bottom of the base section. The body section can include one or more outlets disposed at a height that is greater than or equal to approximately 7 feet with respect to the bottom of the base section. The air sanitation device can include an ultraviolet (UV) light source disposed in an interior of the air sanitation device and can include an air movement device configured to move air into the base section via the one or more inlets, past the UV light source, and out of the body section via the one or more outlets.

The air sanitation device can include a filter at least partially disposed in the interior of the air sanitation device.

The one or more outlets can include an air distribution device configured to direct a flow of discharged air in a downward angle. The downward angle can be between approximately 1 degree and approximately 30 degrees with respect to horizontal.

The one or more outlets can include an air distribution device configured to direct a flow of discharged air in an upward angle. The upward angle can be between approximately 1 degree and approximately 80 degrees with respect to horizontal.

The one or more outlets can be configured to discharge air in a generally horizontal direction.

The air movement device is configured to discharge air between approximately 150 cubic feet per minute (CFM) and approximately 200 CFM.

The base section of the air sanitation device can include one or more inlets configured to draw in air at a height that is within a breathing zone extending between approximately 4.5 feet above ground and approximately 7.2 feet above ground. The body section of the air sanitation device can include one or more outlets configured to discharge air at a height that is greater than or equal to approximately 7 feet above ground.

The air sanitation device can be configured to be installed on the ground, and the one or more inlets can be disposed at a height that is between approximately 4.5 feet and approximately 7.2 feet from a bottom of the base section. The one or more inlets can include at least one of (i) a first inlet disposed at a height that is approximately five feet with respect to the bottom of the base section and (ii) a second inlet disposed at a height that is approximately 7 feet with respect to the bottom of the base section.

The air sanitation device can be configured to be installed on an elevated surface, and the one or more inlets can be disposed at a height that is between approximately 1.5 feet and approximately 2.5 feet from a bottom of the base section. The one or more outlets can be disposed at a height greater than approximately 2.75 feet from the bottom of the base section.

The air movement device can be configured to discharge an airflow between approximately 150 cubic feet per minute (CFM) and approximately 200 CFM.

The disclosed technology includes an air sanitation system. The air sanitation system can include a plurality of air sanitation devices, and the plurality of air sanitation devices can include one or more first air sanitation devices and one or more second air sanitation devices. Each of the first air sanitation devices can include a base section including one or more inlets disposed at a height that is less than or equal to approximately 4.5 feet with respect to a bottom of the base section; a body section including one or more outlets disposed at a height that is greater than or equal to approximately 7 feet with respect to the bottom of the base section; a UV light source disposed in an interior of the air sanitation device; and an air movement device configured to move air into the base section via the one or more inlets, past the UV light source, and out of the body section via the one or more outlets. Each of the second air sanitation devices can include a base section comprising one or more inlets disposed at a height that is within a breathing zone defined as being between approximately 4.5 feet above ground and approximately 7.2 feet above ground; a body section comprising one or more outlets disposed at a height that is greater than or equal to approximately 7 feet with respect to the bottom of the base section; a UV light source; and an air movement device configured to move air into the base section via the one or more inlets, past the UV light source, and out of the body section via the one or more outlets.

The air sanitation system can include one or more floor vent adapters. Each of the floor vent adapters can include an attachment adapter configured to attach to a ceiling return vent and/or a ceiling return duct, a substantially vertically extending duct, and an air intake vent configured to draw in air from a height less than approximately 4.5 feet with respect to ground.

At least one of the plurality of air sanitation devices can be configured to determine a location of another of the plurality of air sanitation devices and output instructions for an air distribution device of the respective air sanitation device to direct a flow of discharged air toward one of more outlets of the other of air sanitation device.

Determining the location of another of the plurality of air sanitation devices can include at least one of (1) receiving a signal from the another of the plurality of air sanitation devices; (2) receiving, from a sensor of the respective air sanitation device, sensor data indicative of a location of another of the plurality of air sanitation devices; and (3) receiving, from a flow sensor of the respective air sanitation device, flow sensor data indicative of a detected airflow. The detected airflow can be indicative of a presence (and/or location) or absence of another air sanitation device that is outputting cleaned air.

Further features and elements of the disclosed technology, and the advantages offered thereby, are explained in greater detail hereinafter with reference to specific examples illustrated in the accompanying drawings, wherein like elements are indicated be like reference designators.

BRIEF DESCRIPTION OF THE DRAWINGS

Reference will now be made to the accompanying drawings, which are not necessarily drawn to scale, are incorporated into, and constitute a portion of, this disclosure, illustrate various implementations and aspects of the disclosed technology and, together with the description, serve to explain the principles of the disclosed technology. In the drawings:

FIGS. 6A and 6B illustrate comparative CFD simulations relating to an indoor environment with and without the disclosed technology, with FIG. 6A illustrating a CFD simulation of the indoor environment without the disclosed technology and FIG. 6B illustrating a CFD simulation of the indoor environment with the disclosed technology.

DETAILED DESCRIPTION

Figure 1:
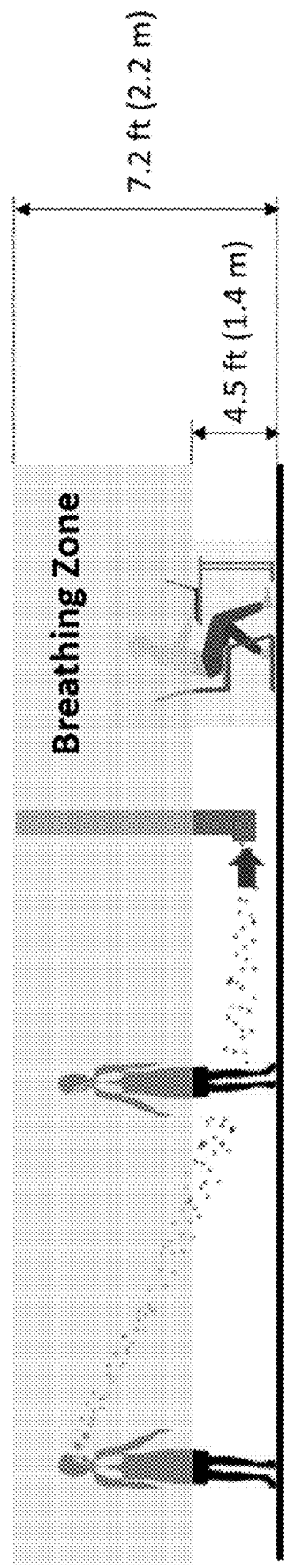
FIG. 1 illustrates the breathing zone for persons in an indoor space, in accordance with the disclosed technology.

Throughout this disclosure, systems and methods are described with respect to air sanitation devices, and air sanitation systems, that can be positioned within a room and are configured to clean, filter, and/or sterilize the air within the breathing zone of an indoor environment. In particular, the disclosed technology can be useful in indoor environments serviced by a HVAC system, although one having skill in the art will recognize that the disclosed technology can be applicable to multiple scenarios and applications.

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Indeed, it is to be understood that other examples are contemplated. Many suitable components that would perform the same or similar functions as components described herein are intended to be embraced within the scope of the disclosed electronic devices and methods. Such other components not described herein may include, but are not limited to, for example, components developed after development of the disclosed technology.

Throughout this disclosure, various aspects of the disclosed technology can be presented in a range format (e.g., a range of values). It should be understood that such descriptions are merely for convenience and brevity and should not be construed as an inflexible limitation on the scope of the disclosed technology. Accordingly, the description of a range should be considered to have specifically disclosed all the possible subranges as well as individual rational numerical values within that range. For example, a range described as being "from 1 to 6" includes the values 1, 6, and all values therebetween. Likewise, a range described as being "between 1 and 6" includes the values 1, 6, and all values therebetween. The same premise applies to any other language describing a range of values. That is to say, the ranges disclosed herein are inclusive of the respective endpoints, unless otherwise indicated.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Although the disclosed technology may be described herein with respect to various systems and methods, it is contemplated that embodiments or implementations of the disclosed technology with identical or substantially similar features may alternatively be implemented as methods or systems. For example, any aspects, elements, features, or the like described herein with respect to a method can be equally attributable to a system. As another example, any aspects, elements, features, or the like described herein with respect to a system can be equally attributable to a method.

Reference will now be made in detail to example embodiments of the disclosed technology, examples of which are illustrated in the accompanying drawings and disclosed herein. Wherever convenient, the same reference numbers will be used throughout the drawings to refer to the same or like parts.

As explained above, certain HVAC systems are designed to filter and/or sanitize air passing therethrough such that filtered and/or sanitized air can be provided to a conditioned space. However, this does nothing to address pathogens introduced directly into the air within the conditioned space itself. Moreover, existing systems typically attempt to clean, filter, and/or sterilize all of the air within a space (e.g., a room, a conditioned space), which is typically not practicable due at least to the introduction of pathogens by persons located within the space. Moreover, many airborne pathogens, such as COVID-19, must be inhaled or ingested by a person for that person to contract the disease. Thus, transmission of such pathogens can be prevented, mitigated, and/or slowed by decreasing the amount and/or prevalence of the pathogen in areas surrounding the faces of people within the space. This can decrease the volume of space in which the air must be cleaned, filtered, and/or sterilized, while still providing an increased effectiveness of disease transmission prevention. Stated otherwise, instead of attempting to clean all of the area within a given room, it is possible to decrease and/or minimize pathogen transmission by treating only a particular, targeted portion of the room that corresponds to the faces of the people located within the room. Referring to FIG. 1, such a particular, targeted portion of a room can be referenced as the breathing zone. As an example, the breathing zone can correspond to the volume with a room that exists from approximately 4.5 feet (approximately 1.4 meters) from the floor to approximately 7.2 feet (approximately 2.2 meters) from the floor.

Figure 2A:
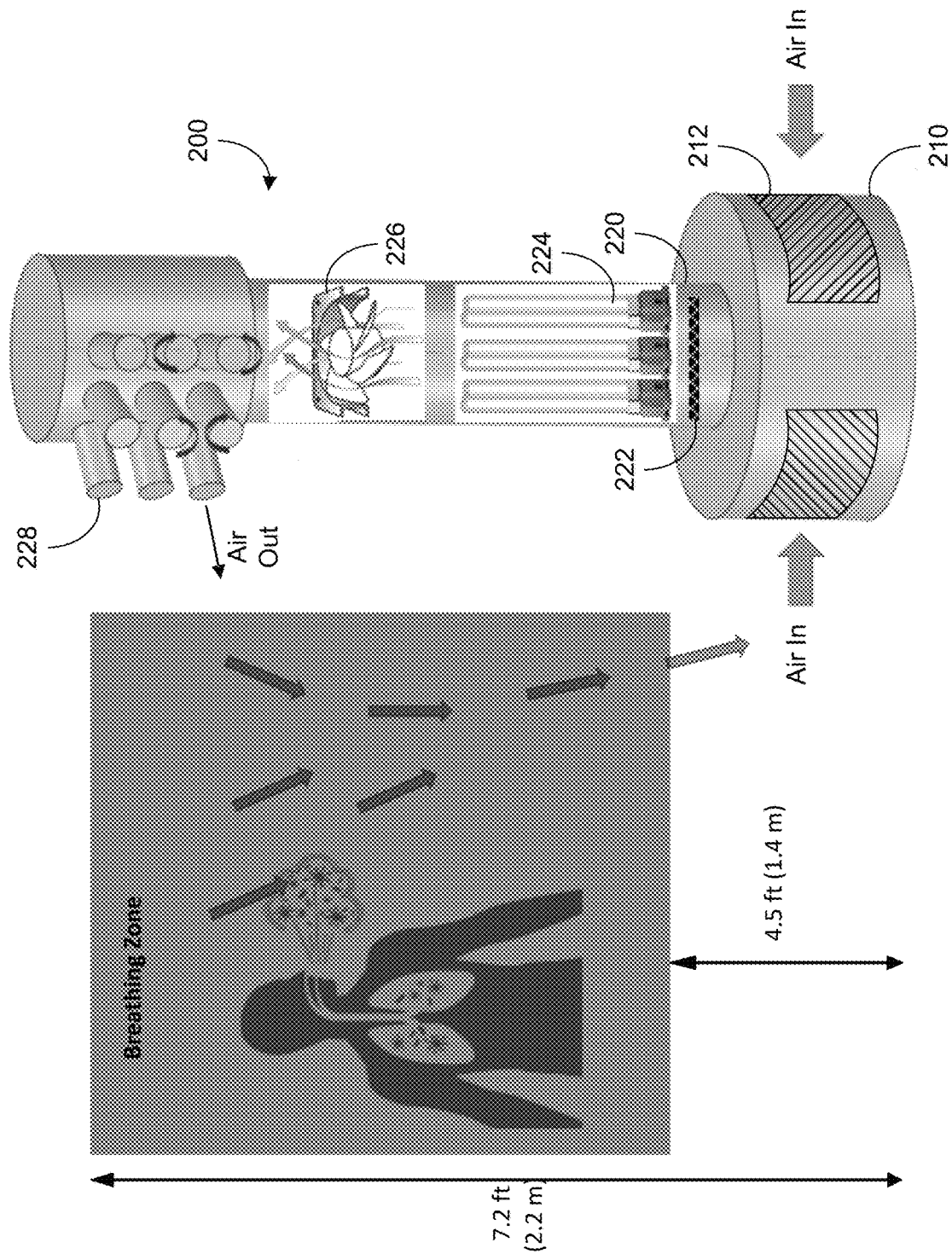
FIGS. 2A-4C illustrate example air sanitation devices, in accordance with the disclosed technology.
Figure 2B:
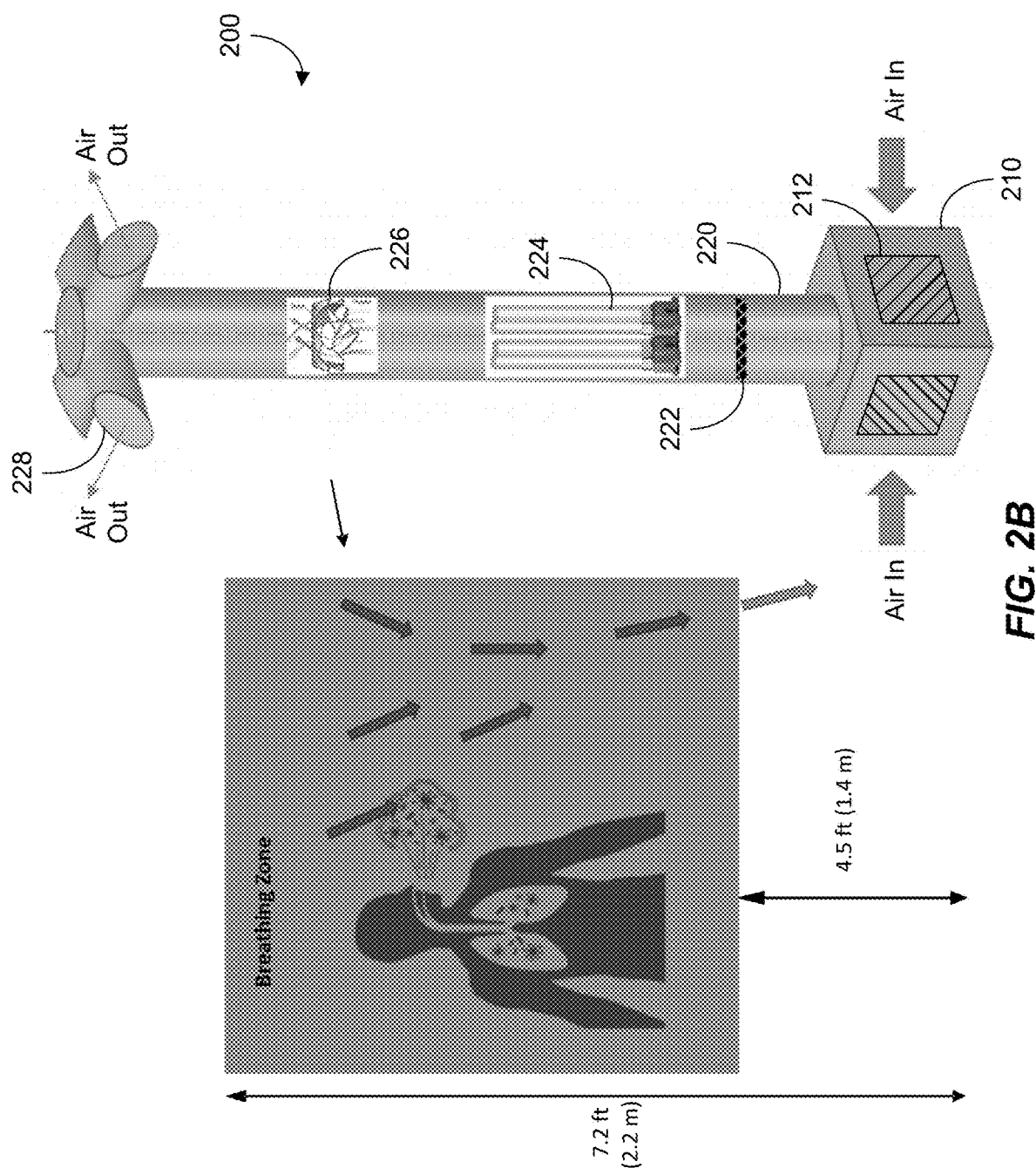
Figure 2C:
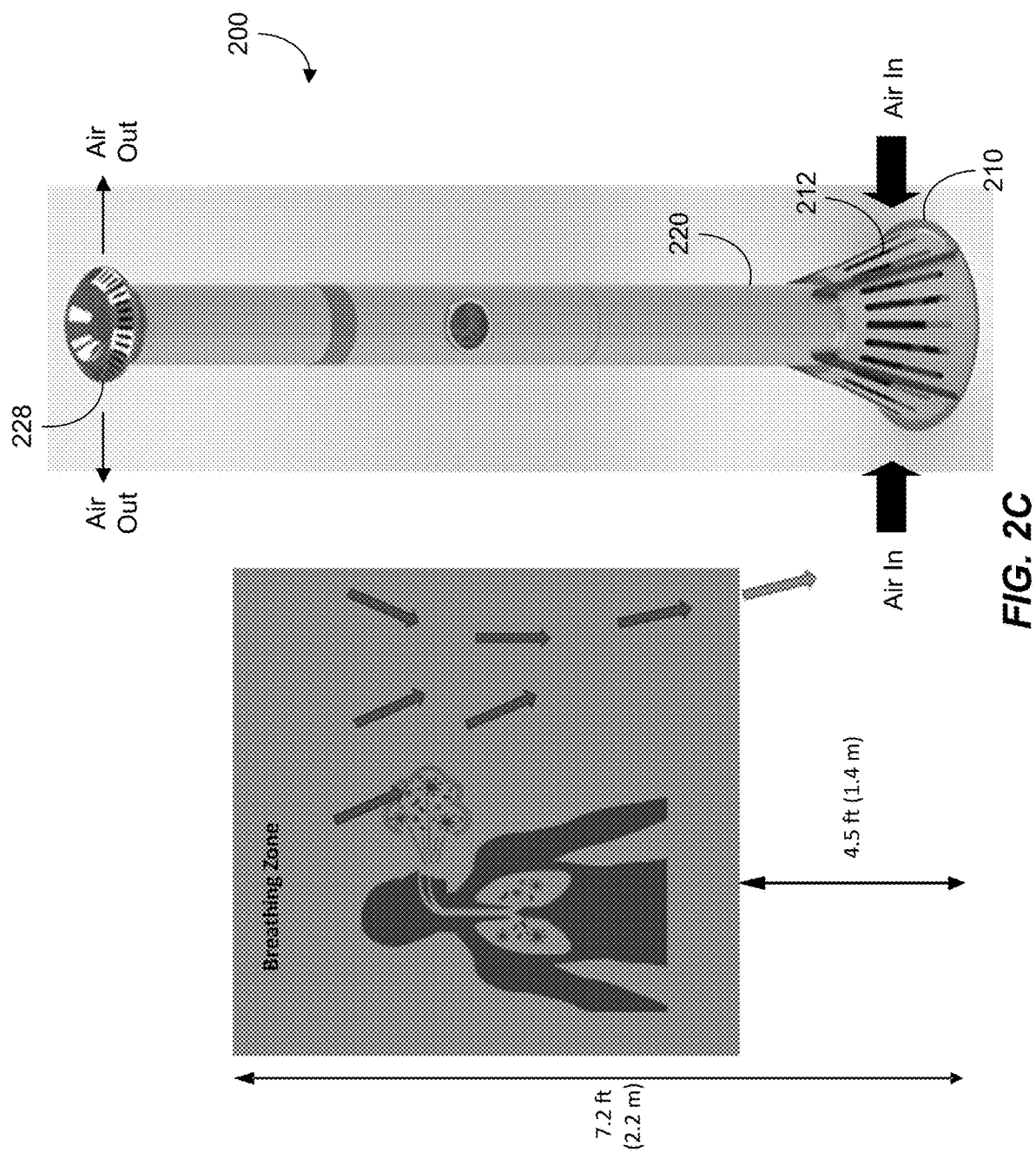

The disclosed technology includes air sanitation devices and/or air sanitation systems that can be positioned within a room and is/are configured to clean, filter, and/or sterilize the air within the breathing zone. Referring to FIGS. 2A-2C, example air sanitation devices 200 are illustrated. The disclosed air sanitation device 200 can be freestanding (e.g., configured to be placed on a floor). The air sanitation device 200 can include a base section 210 and a body section 220. The air sanitation device 200 can be configured to draw in air proximate the bottom section 210 and discharge cleaned air proximate the top of the body section 220. As shown, the body section 220 can be substantially elongate and substantially tubular. Alternatively, the body section 220 can have any shape.

Optionally, the base section 210 can include wheels (not shown), which can help facilitate easy movement and positioning of the air sanitation device 200. One or more of the wheels can be motor driven, which can further facilitate easy movement and positioning of the air sanitation device 200. The base section can include one or more inlets 212 through which air can be drawn from the surrounding environment and into the air sanitation device 200.

The body section 220 can include a filter 222 and/or an ultraviolet (UV) light source 224 (e.g., UV-C). The UV light sources 224 can include an array of multiple UV light sources 224 positioned to expose all or substantially all of any passing air to UV radiation. For example, the UV light sources 224 can be spaced about the perimeter of the inner wall of the body section 220 and configured to direct UV light inwardly such that passing air is exposed to the UV light. Alternatively or additionally, one or more UV light sources 224 can be located at or near the center of the body section and can be configured to direct UV light outwardly such that passing air is exposed to the UV light. The central UV light source(s) 224 can form a substantially cylindrical shape, a substantially spherical shape, a substantially polygonal shape, or any other shape. Alternatively or additionally, the UV light source 224 can be arranged to form a helical flow path (e.g., a helically arranged array of UV light sources 224), which can help increase the exposure time of passing air to outputted UV radiation, while decreasing the overall size of the UV light source portion of the air sanitation device 200. To help ensure all or substantially all of the passing air is exposed to UV radiation, reflective material or a reflective coating can be disposed on the inner wall of the body section 220 proximate the UV light source(s) 224. The body section can include 220 one or more air movement devices 226, which can include a blower, a fan, an induction fan, a variable speed fan, or any other device configured to draw in and/or push air. While the filter 222, UV light sources 224, and air movement device 226 are shown as being disposed within the body section, one, some, or all of these components can be located in different portions of the air sanitation device 200 (e.g., in the base section 210). Further, the various components can be provided in a sequential order different from that illustrated in FIGS. 2A and 2B.

After air passes through the filter 222 and/or the UV light source(s) 224, the air movement device 226 can push the cleaned air out of the air sanitation device 200 and back into the surrounding environment. The cleaned air can be discharged via one or more outlets 228. As shown in FIGS. 2A and 2B, the outlets 228 can include outlet tubes that project radially outward from an upper portion of the body section 220. Alternatively or additionally, some or all of the outlets 228 can omit any corresponding outlet tube. Outlets 228 can be provided at a single area of the air sanitation device 200 (e.g., a single side of the air sanitation device 200 as shown in FIG. 2A). Alternatively, outlets 228 can be provided about the entire perimeter of the air sanitation device 200 or at predetermined positions about the perimeter of the air sanitation device (e.g., equidistantly spaced about the perimeter of the air sanitation device 200 as shown in FIG. 2B). The outlets 228 can be located at a height that is at, near, or above the top of the breathing zone, such as at a height that is greater than or equal to approximately 7 feet. For example, the outlets 228 can be located at a height that is in a range from approximately 7 to approximately 12 feet, with respect to the ground. As will be appreciated, discharging air from a high position that is at, near, or above the top of the breathing zone can help create a downflow effect that will push aerosols out of the breathing zone.

Referring to FIG. 2A, one or more of the outlets 228 can be configured to discharge the cleaned air at a downward angle (e.g., via an air distribution device comprising one or more louvers, one or more dampers, or the like). For example, the outlets 228 can be configured to discharge the cleaned air at a downward angle that is in a range from approximately 5 degrees to approximately 30 degrees. A given outlet 228 can include one or more air distribution devices (e.g., one or more lovers, dampers, vanes, or foils) configured to direct the cleaned air in a desired direction. The downward angle of the discharged air can help create the downflow effect. The outlets 228 can be arranged such that adjacent outlets discharge cleaned air in opposite rotational directions (e.g., via one or more internal radial swirl vanes in a given outlet 228).

Alternatively or additionally, and referring to FIG. 2B, one or more of the outlets 228 can be configured to discharge the cleaned air at an upward angle. Such a configuration can, for example, be configured to use a ceiling of the room in which the air sanitation device 200 is located to help guide flow of discharged air. That is, the cleaned air can be discharged upwardly toward a ceiling to rebound the ceiling at a desired angle to create a desired downward flow effect. This can, in some instances, enable air to flow or glide a longer lateral distance, instead of the discharged air quickly falling toward the ground. This can, in turn, ultimately enable a downward effect that can efficiently push pathogens out of the breathing zone. As a non-limiting example, the outlets 228 can be configured to discharge the cleaned air at an upward angle that is in a range from approximately 1 degree to approximately 80 degrees. As a more specific example, the outlets 228 can be configured to discharge the cleaned air at an upward angle of approximately 45 degrees. A given outlet 228 can include one or more air distribution devices (e.g., one or more louvers, dampers, vanes, or foils) configured to direct the cleaned air in a desired direction. The downward angle of the discharged air can help create the downflow effect. The outlets 228 can optionally be arranged such that adjacent outlets discharge cleaned air in opposite rotational directions (e.g., via one or more internal radial swirl vanes in a given outlet 228). To ensure the air rebounds off the ceiling at the angle, the air sanitation device 200 can be configured such that the outlets 228 are positioned or positionable at a height that is in a range from approximately 0.5 feet to approximately 2 feet less than the height of the ceiling of the room in which the air sanitation device 200 is located. Since typical residential rooms and office spaces have a ceiling height in the range from approximately 9 feet to approximately 14 feet, the air sanitation device 200 can be configured such that the outlets 228 are positioned or positionable at a height that is in a range from approximately 7 feet to approximately 12 feet. That being said, it is contemplated that the outlets 228 can be positioned or positionable at heights outside of this particular range.

Alternatively or additionally, the one or more of the outlets 228 can be configured to discharge the cleaned air at a substantially horizontal direction (i.e., 0 degrees with respect to horizontal). For example, referring now to FIG. 2C, the air sanitation device 200 can be configured to discharge air from one or more outlets 228 located proximate the top of, or above, the breathing zone (e.g., proximate the top of the body section 220), and the outlet(s) 228 can be configured to discharge cleaned air in a generally horizontal direction. The one or more outlets 228 can comprise slots disposed in an outer wall of a discharge portion of the air sanitation device 200. The outlet(s) 228 can be situated about the entire perimeter of the discharge portion. Alternatively, the outlet(s) 228 can be located in one or more particular regions of the discharge portion, which can help effect discharge of cleaned air in a desired direction. For example, the outlet(s) 228 can be located in a section comprising approximately 25% of the discharge portion's perimeter. As another example, the outlet(s) 228 can be located in a section comprising approximately 50% of the discharge portion's perimeter. Additionally or alternatively, one or more dampers can be included. Each damper can be opened to permit the discharge of cleaned air through one or more particular outlets 228, or the damper can be closed to partially or fully cover one or more particular outlets 228 to prevent or inhibit the discharge of cleaned air through the one or more particular outlets 228.

As will be appreciated, air sanitation devices 200 providing upward discharge angles can be particularly useful for large, open spaces (e.g., open office spaces) in which it is desirable for the cleaned air to travel relatively long distances. On the other hand, air sanitation devices 200 providing downward discharge angles can be particularly useful for smaller spaces (e.g., an individual office) in which it is unnecessary for the cleaned air to travel relatively long distances.

The air movement device 226 can be configured to output air at a velocity that is less than approximately 5 ft/s, which can help avoid the creation of recirculation flows and elevations gains of the discharged air. For example, the air movement device 226 can be configured to output air at a velocity that is in a range from approximately 1 ft/s to approximately 5 ft/s. Alternatively or additionally, the air movement device 226 can be configured to output an airflow between approximately 150 cubic feet per minute (CFM) and approximately 200 CFM. As a more specific example, the air movement device 226 can be configured to output an airflow of approximately 175 CFM.

The air sanitation device 200 can have an adjustable height. For example, the air sanitation device can be configured to telescopically adjust its height (e.g., as illustrated in FIG. 3B). As a non-limiting example, the top of the air sanitation device 200 can be adjustable to heights from approximately 7 feet to approximately 10 feet. The air sanitation device 200 can be configured to be manually adjusted to different heights. Alternatively or additionally, the air sanitation device 200 can include one or more motors configured to adjust the height of the air sanitation device 200, according to a user input such as from an integrated user input interface, a mobile device, or some other computing device. Optionally, the air sanitation device 200 can include one or more sensors (not shown) configured to detect the presence of persons within a predetermined area surrounding the air sanitation device 200. The sensor(s) can include one or more of an acoustic sensor, a camera used with image recognition methods, an infrared sensor, radar, lidar, detection of a mobile device associated with one or more persons (e.g., a Bluetooth, Wi-Fi or other signal associated with a mobile device and/or a computing device associated with a person), a motion sensor, a proximity sensor, or the like. Alternatively or additionally, the one or more sensors can be configured to determine a height of persons in the predetermined area. Based on the presence and/or height of the persons located within the predetermined distance, the air sanitation device 200 can be configured to engage/disengage the UV light source 224 and/or air movement device 226 and/or automatically adjust the current height of the air sanitation device 200. For example, the air sanitation device 200 can be configured to disengage the UV light source 224 and air movement device 226 if no persons are located in the predetermined area or if no person has been located in the predetermined area for a predetermined time. Alternatively or additionally, the air sanitation device 200 can be configured to disengage the UV light source 224 and air movement device 226 at a scheduled time, day, or date. Conversely, the air sanitation device 200 can be configured to engage the UV light source 224 and air movement device 226 if a person has entered the predetermined area. Alternatively or additionally, the air sanitation device 200 can be configured to engage the UV light source 224 and air movement device 226 at a scheduled time, day, or date.

As another example, the air sanitation device 200 can be configured to increase the current height of the air sanitation device 200 if a person who is taller than a predetermined height threshold enters the predetermined area. Alternatively or additionally, the downward angle of one or more outlets 228 can be adjusted depending on the height of one or more persons located within the predetermined area. The air sanitation device 200 can be configured to adjust the downward angle of outlets located on a side of the air sanitation device 200 where the corresponding person is located. As will be appreciated, the breathing zone corresponds to persons having a height within a certain range. Thus, if a person who is shorter or taller than the heights covered by the breathing zone, the air sanitation device 200 can automatically adjust its height and/or downward angle of one or more outlets 228 to help direct clean air into a desired area relative that person (e.g., direct clean air toward the face of that person).

Similarly, the air sanitation device 200 can be configured to increase or decrease the flow speed of discharged air depending on the detected presence and/or location of persons relative the air sanitation device 200. For example, a person located relatively far from the air sanitation device 200 can benefit from an increased flow speed, which can increase the likelihood that clean air will reach that person's location. As another example, a person located relatively near the air sanitation device 200 can benefit from a decreased flow speed, which can increase the likelihood that clean air will reach that person's location. As mentioned above, the air movement device 226 can include a variable speed fan, which help facilitate the adjustability of flow speed. Further, there may be some limits on discharge speed corresponding to the exposure time of air passing the UV light source(s) 224, but such limits could be mitigated by, for example, including a helical arrangement of UV light source(s) 224.

The air sanitation device 200 can include one or more sensors configured to detect the presence of aerosols in the air, which can include a radiometer, an infrared sensor, an optical counting sensor (e.g., based upon either light scattering, light obscuration, and/or direct imaging), a condensation particle counter, a differential mobility particle sizer (e.g., a scanning mobility particle sizer, a fast mobility particle sizer), or the like. The air sanitation device 200 can be configured engage/disengage the UV light source 224 and/or air movement device 226 based on the presence and/or concentration or aerosols in the air. For example, if the detected concentration of aerosols is above a first predetermined threshold, the air sanitation device 200 can be configured engage the UV light source 224 and/or air movement device 226, and if the detected concentration of aerosols is less than or equal to a second predetermined threshold, the air sanitation device 200 can be configured disengage the UV light source 224 and/or air movement device 226. The first and second predetermined threshold can be the same threshold. Alternatively, the first predetermined threshold can be different from the second predetermined threshold. For example, the first predetermined threshold can be less than the second predetermined threshold. Conversely, the first predetermined threshold can be greater than the second predetermined threshold.

Moreover, the air sanitation device 200 can be configured to adjust the power and/or speed of the air sanitation device 200 based on the detected concentration of aerosols. For example, the air sanitation device 200 can increase the power and/or speed (e.g., of the air movement device 226) if the detected concentration of aerosols is high, and the air sanitation device 200 can decrease the power and/or speed if the detected concentration of aerosols is relatively lower but still above at least one of the first or second predetermined thresholds.

The air sanitation device 200 can include a display and/or a speaker and can be configured to output alerts corresponding to the detected aerosol concentration. For example, the air sanitation device 200 can output an audible alarm if the aerosol concentration is above a predetermined threshold, and/or the air sanitation device 200 can provide a visual display (e.g., via a display screen, a light indicator) indicating an alert associated with the detected aerosol concentration. If the aerosol concertation is greater than a danger threshold, the air sanitation device 200 can output an alarm warning persons to evacuate the room, and once the air sanitation device 200 detects an aerosol concentration that is below a safety threshold, the air sanitation device 200 can output a message indicating that it is safe to reenter the room. The air sanitation device 200 can output various messages to mobile devices or computing devices of users associated with the air sanitation device 200. Alternatively or additionally, the air sanitation device can output messages to mobile devices or computing devices within a message range of the air sanitation devices. For example, the air sanitation device 200 can broadcast a beacon signal comprising one or more messages (e.g., via Bluetooth, Bluetooth Low Energy).

Figure 3A:
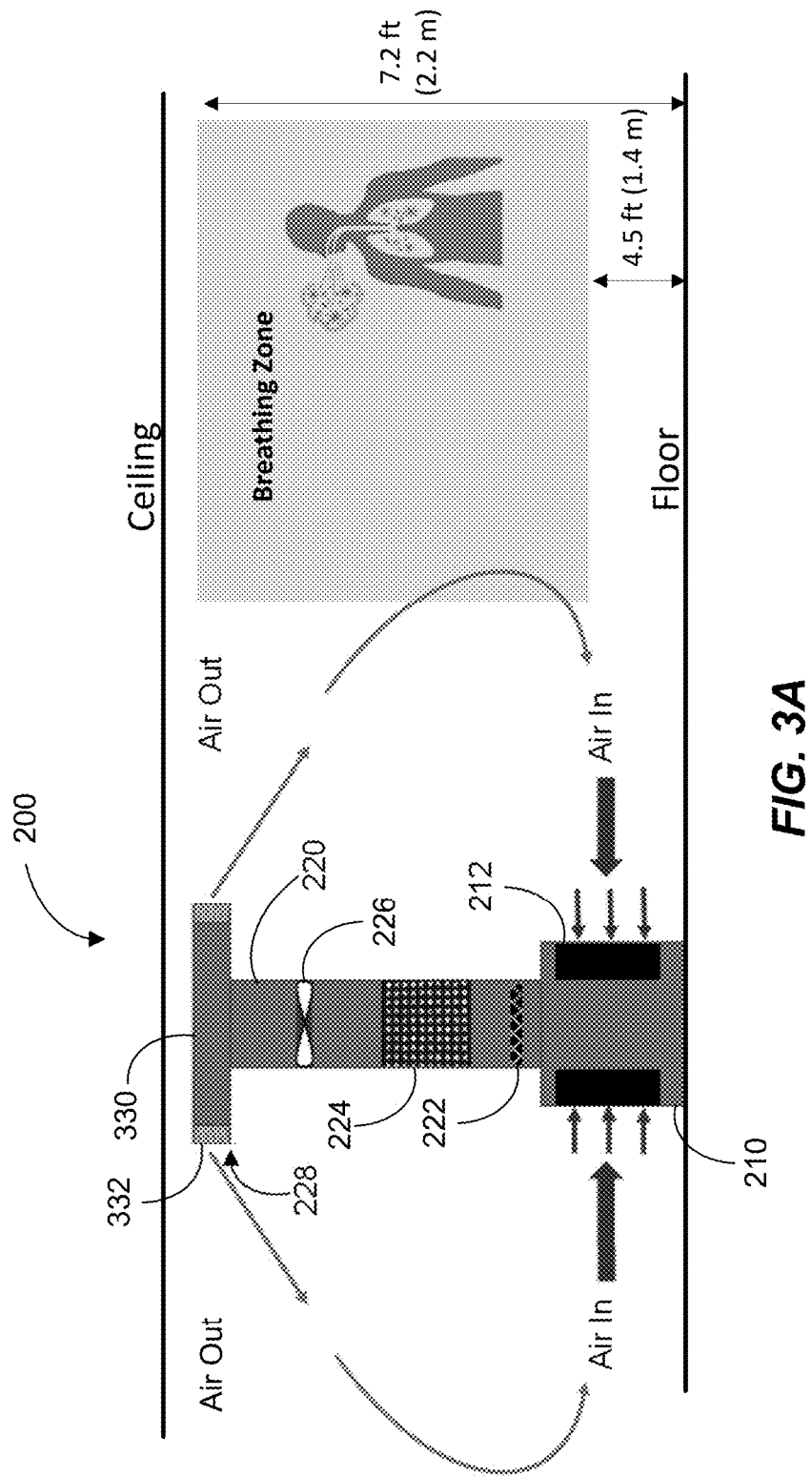
Figure 3B:
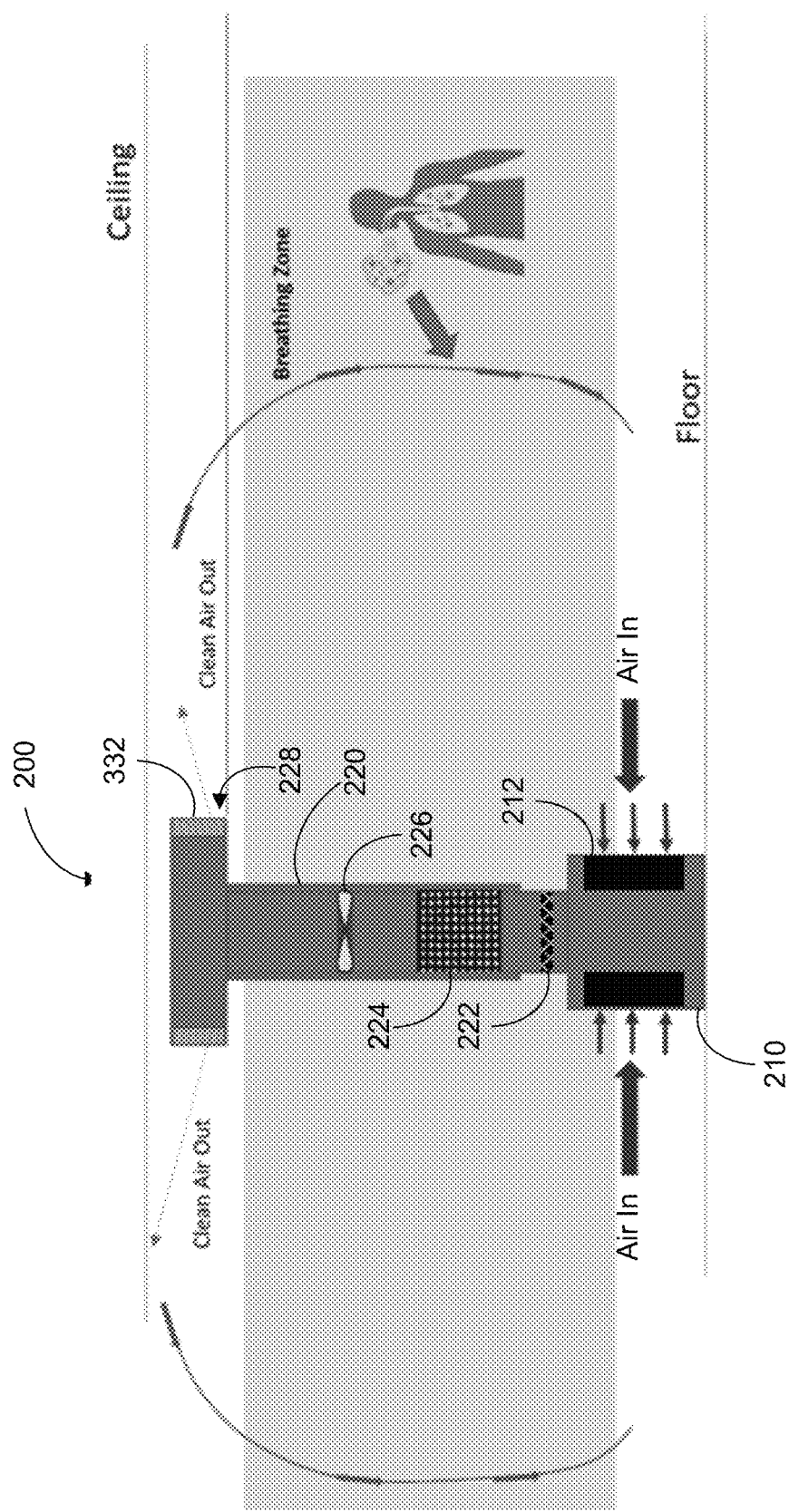

Referring to FIGS. 3A and 3B, the air sanitation device 200 can include a top section 330. The top section 330 can have a substantially disk shape. The top section can include one or more outlets 228 disposed at or near an outer edge of the top section 330. The outlet(s) 228 disposed on the top section 330 can include a plurality of diffuser plates 332, which can direct the flow of cleaned air from the top section 330. As an example and referring to FIG. 3A in particular, the diffuser plates 332 can have a downward angle (e.g., in a range from approximately 5 degrees to approximately 30 degrees). All of the diffuser plates 332 can have the same downward angle. Alternatively, some of the diffuser plates 332 can have a downward angle that is different from the downward angle of some of the other diffuser plates 332. For example, a first side of the top section 330 can include diffuser plates 332 having a first downward angle, and a second side of the top section 330 can include diffuser plates 332 having a second downward angle.

Alternatively or additionally, one or more of the diffuser plates 332 can be configured to discharge the cleaned air at a substantially horizontal direction (i.e., 0 degrees with respect to horizontal). Alternatively or additionally, and referring to FIG. 3B in particular, one or more of the diffuser plates 332 can be configured to discharge the cleaned air at an upward angle. As described above, such a configuration can, for example, be configured to use a ceiling of the room in which the air sanitation device 200 is located to help guide flow of discharged air. As a non-limiting example, the diffuser plates 332 can be configured to discharge the cleaned air at an upward angle that is in a range from approximately 1 degree to approximately 80 degrees. As a more specific example, the diffuser plates 332 can be configured to discharge the cleaned air at an upward angle of approximately 45 degrees. To ensure the air rebounds off the ceiling at the angle, the air sanitation device 200 can be configured such that the outlets 228 are positioned or positionable at a height that is in a range from approximately 0.5 feet to approximately 2 feet less than the height of the ceiling of the room in which the air sanitation device 200 is located. Since typical residential rooms and office spaces have a ceiling height in the range from approximately 9 feet to approximately 14 feet, the air sanitation device 200 can be configured such that the outlets 228 are positioned or positionable at a height that is in a range from approximately 7 feet to approximately 12 feet. That being said, it is contemplated that the outlets 228 can be positioned or positionable at heights outside of this particular range. Some of the diffuser plates 332 can have an upward angle that is different from the upward angle of some of the other diffuser plates 332. For example, a first side of the top section 330 can include diffuser plates 332 having a first upward angle, and a second side of the top section 330 can include diffuser plates 332 having a second upward angle. As another example, some diffuser plates 332 can have a downward angle while other diffuser plates can have an upward angle.

Some or all of the diffuser plates 332 can be fixed. Alternatively or additionally, some or all of the diffuser plates 332 can be moveable. Some or all of the diffuser plates 332 can be in communication with one or motors (not shown) configured to automatically adjust the downward angle of at least some of the diffuser plates 332. For example, the diffuser plates 332 can be adjusted similar to the methods and processes by which the outlet tubes discussed above can adjusted (e.g., based on the detected height of a person in the predetermined area).

Referring in particular to FIGS. 2A-3B, the disclosed technology can simultaneously suppress and dilute pathogens and/or infections particles present in the air of an indoor environment. As will be appreciated, locating the inlet(s) 212 below the bottom of the breathing zone can help create a downward flow arrangement of air within the indoor environment; this can result in suppression of suspended aerosols in the air by drawing the suspended aerosols toward the inlet(s) 212 and thus toward ground level, thereby removing the aerosols from the breathing zone. After intake, the air can be exposed to UV light, which can kill pathogens and sanitize the air. The sanitized air can be discharged at, near, or above the top of the breathing zone, and the sanitized air can be discharged at a downward angle. Introducing sanitized air into the indoor environment can help dilute the aerosols. The downward flow of the discharged, sanitized air from a high position can help suppress aerosols by pushing them downward toward the ground and out of the breathing zone. With the aerosols pushed to ground level, the air including the aerosol can be drawn into the inlet(s) 212, repeating the process. Moreover, the outlets 228 can be outfitted such that adjacent outlets 228 output air in opposing swirl directions. This can result in perturbation of the shear layer and can enhance mixing between the sanitized air and untreated air in the indoor environment, thereby further diluting the aerosols.

Due at least in part to the location of air intake, the height of the air sanitation device 200, and/or the location of cleaned air discharge, the air sanitation device 200 can be particularly well suited for cleaning air in open areas, such as open or shared office spaces, hallways, and the like.

Figure 4A:
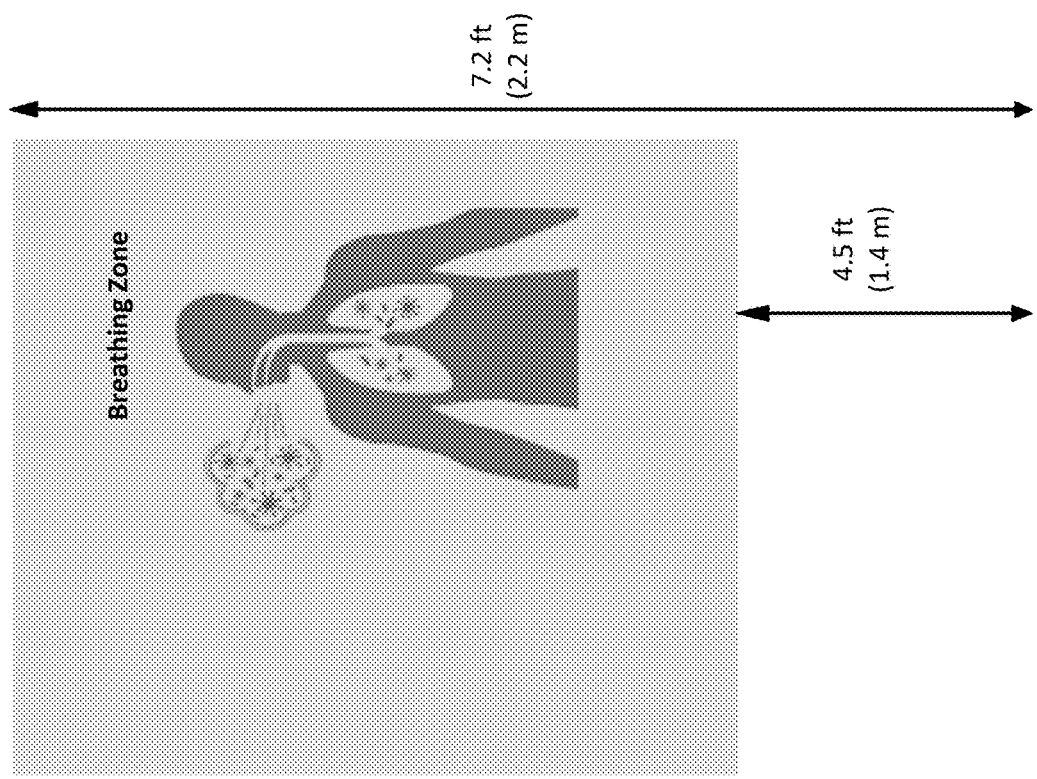
Figure 4A:
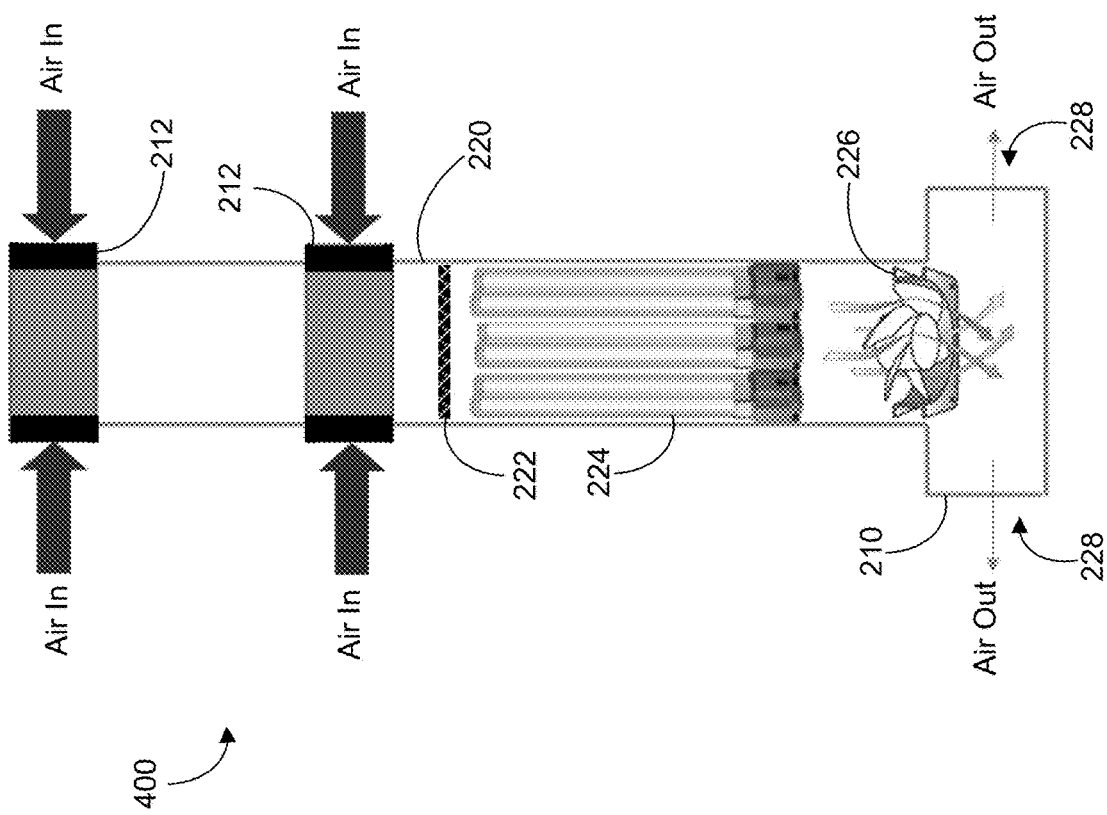
Figure 4B:
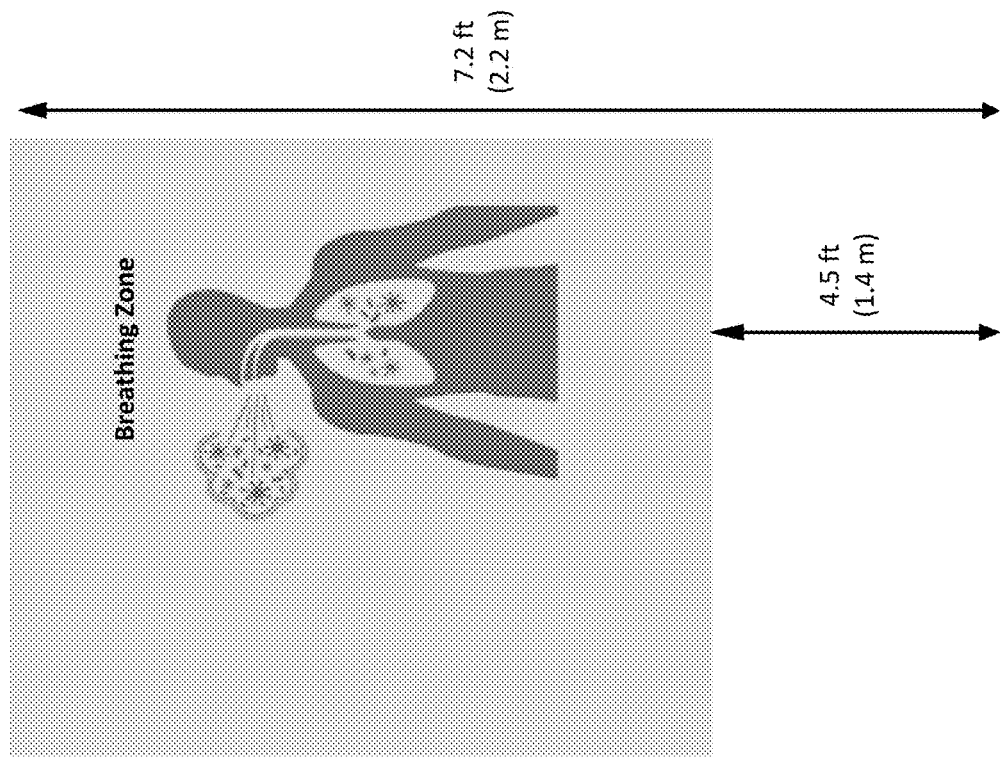
Figure 4B:
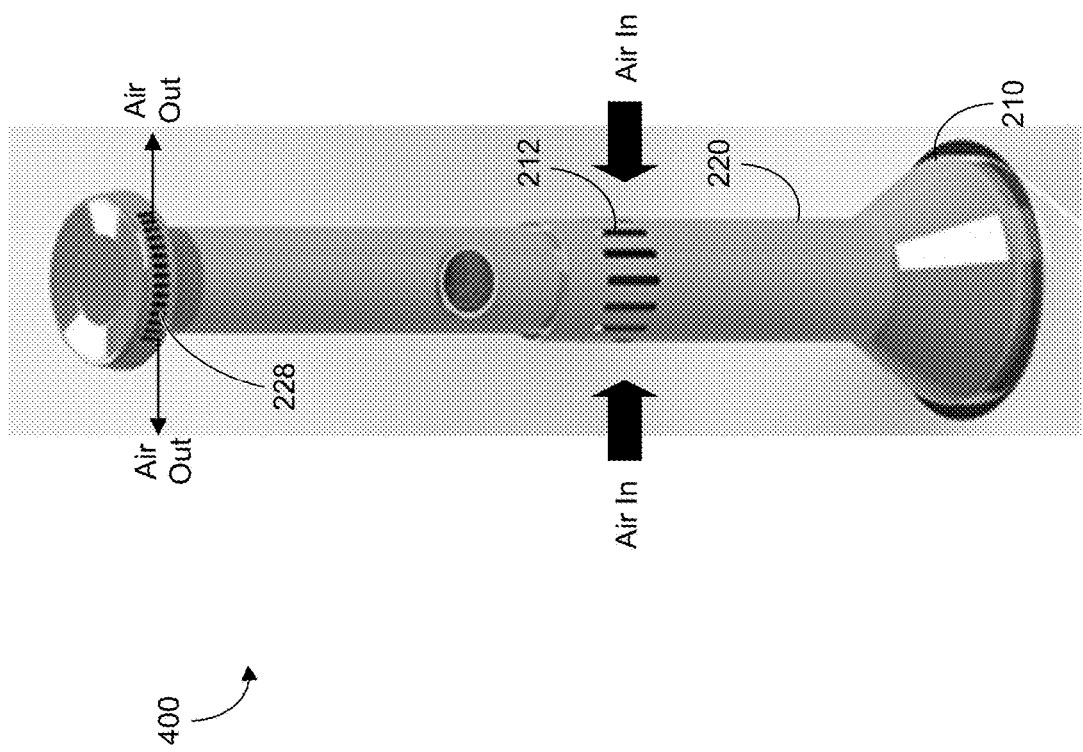
Figure 4C:
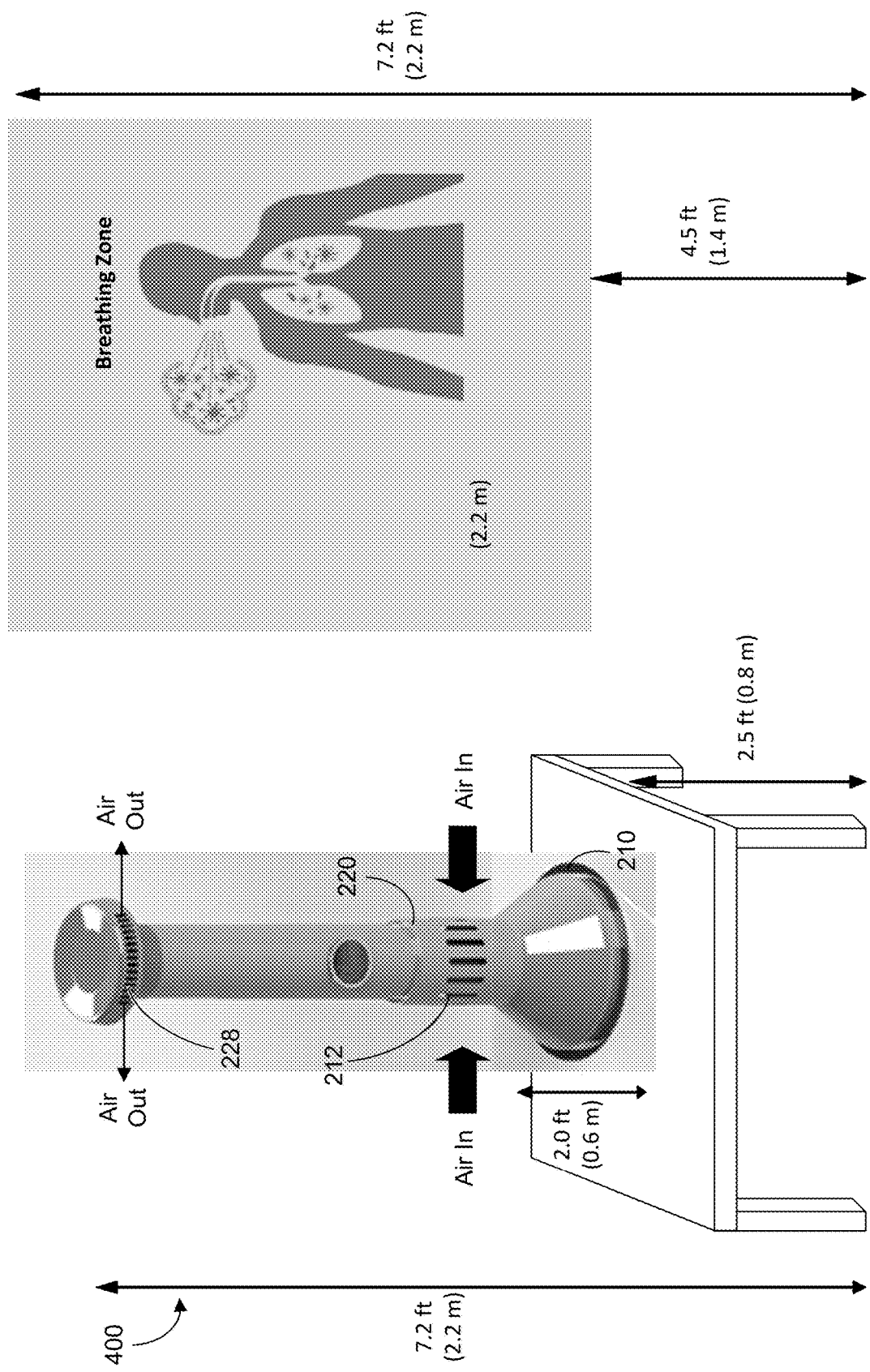

As disclosed above, the air sanitation device 200 can be configured to draw air inwardly proximate the bottom section 210 and discharge air proximate the top of the air sanitation device 200. The disclosed technology is not so limited, however. Referring to FIGS. 4A-4C, the disclosed technology include an air sanitation device 400 configured to draw in air at one or more inlets 212 that are disposed proximate a middle portion and/or a top portion of the air sanitation device 400, and the air sanitation device 400 can be configured to discharge air proximate a bottom portion of the air sanitation device 400 (e.g., the base section 210). The inlet(s) 212 of the air sanitation device 400 can be located at one or more heights that are within the breathing zone. For example, a lower inlet 212 can be located at approximately 5 feet from ground and an upper inlet 212 can be located at approximately 7 feet from ground. Thus, the air sanitation device 400 can be configured to draw in aerosols and/or microdroplets before the aerosols and/or microdroplets leave (e.g., initially leave) the breathing zone. Thus, circulation of air exhaled from a person can be caught by the air sanitation device 400 before it becomes circulated about the space, thereby reducing the amount of travel experienced by a given microdroplet. This can decrease the likelihood that another person will inhale or ingest the microdroplet. The air movement device 226 can move air from the inlet(s) 212 and downwardly through the body section 220. The air movement device 226 can move air through the filter 222 and/or through or past the UV light source(s) 224. The air movement device 226 can then push cleaned air out of the air sanitation device 400 via outlets 228. The outlets 228 can be located at a height that is less than the bottom of the breathing zone, such as less than approximately 4.5 feet. For example, the outlets 228 can be located at a height that is less than or equal to approximately 2 feet above the ground. As another example, the outlets 228 can be located at a height that is less than or equal to approximately 1 foot above the ground. The outlets 228 can discharge the cleaned air in a substantially horizontal direction. Alternatively, the outlets can discharge the cleaned air in an upward direction (e.g., via an air distribution device comprising one or more louvers, one or more dampers, or the like), such as in a direction having an upward angle in the range from approximately 5 degrees to approximately 15 degrees, with respect to horizontal. Any additional elements described with respect to the air sanitation device 200 can be incorporated into the air sanitation device 400, taking into consideration the fact that the air sanitation device 400 is oriented in a substantially opposite configuration as compared to air sanitation device 200. The air movement device 226 can be configured to output air at a velocity that is less than approximately 5 ft/s, which can help avoid the creation of recirculation flows and elevations gains of the discharged air. For example, the air movement device 226 can be configured to output air at a velocity that is in a range from approximately 1 ft/s to approximately 5 ft/s. As a more specific example, the air movement device can be configured to output air at approximately 2 ft/s. Alternatively or additionally, the air movement device 226 can be configured to output airflow between approximately 50 CFM and approximately 100 CFM. As a more specific example, the air movement device 226 can be configured to output an airflow between approximately 70 CFM and approximately 75 CFM.

Referring in particular to FIGS. 4A and 4B, the air sanitation device 400 can be configured to draw in air from the breathing zone (e.g., at a height between approximately 4.5 feet and approximately 5 feet relative the ground) and discharge air from one or more outlets 228 located proximate the top of, or above, the breathing zone (e.g., proximate the top of the body section 220). As explained above, the outlet(s) 228 can be configured to discharge cleaned air in a generally horizontal direction. The one or more outlets 228 can comprise slots disposed in an outer wall of a discharge portion of the air sanitation device 400. The outlet(s) 228 can be situated about the entire perimeter of the discharge portion. Alternatively, as illustrated in FIGS. 4B and 4C, the outlet(s) 228 can be located in one or more particular regions of the discharge portion, which can help effect discharge of cleaned air in a desired direction. For example, the outlet(s) 228 can be located in a section comprising approximately 25% of the discharge portion's perimeter, as illustrated in FIGS. 4B and 4C. As another example, the outlet(s) 228 can be located in a section comprising approximately 50% of the discharge portion's perimeter. Additionally or alternatively, one or more dampers can be included. Each damper can be opened to permit the discharge of cleaned air through one or more particular outlets 228, or the damper can be closed to partially or fully cover one or more particular outlets 228 to prevent or inhibit the discharge of cleaned air through the one or more particular outlets 228.

FIG. 4B illustrates an example air sanitation device 400 configured to be installed on the ground, and FIG. 4C illustrates an example air sanitation device 400 configured to be installed on a desk, table, or other surface. As will be appreciated, the height of a table or desk is typically between approximately 28 inches and approximately 30 inches. Therefore, to maintain the position of the air intake within the breathing zone, the inlet(s) 212 can be located near the bottom of the air sanitation device 400. For example, the inlet(s) 212 can be located between approximately 1.5 feet and approximately 2.5 feet above the bottom of the air sanitation device 400. Similarly, the outlet(s) 228 can be located at a position to account for the height of the table, desk, or other surface that is elevated with respect to the ground. For example, the outlet(s) 228 can be located at a height greater than approximately 2.75 feet. As more specific example, the outlet(s) 228 can be located at a height between approximately 2.75 feet and approximately 9.5 feet.

Figure 5A:
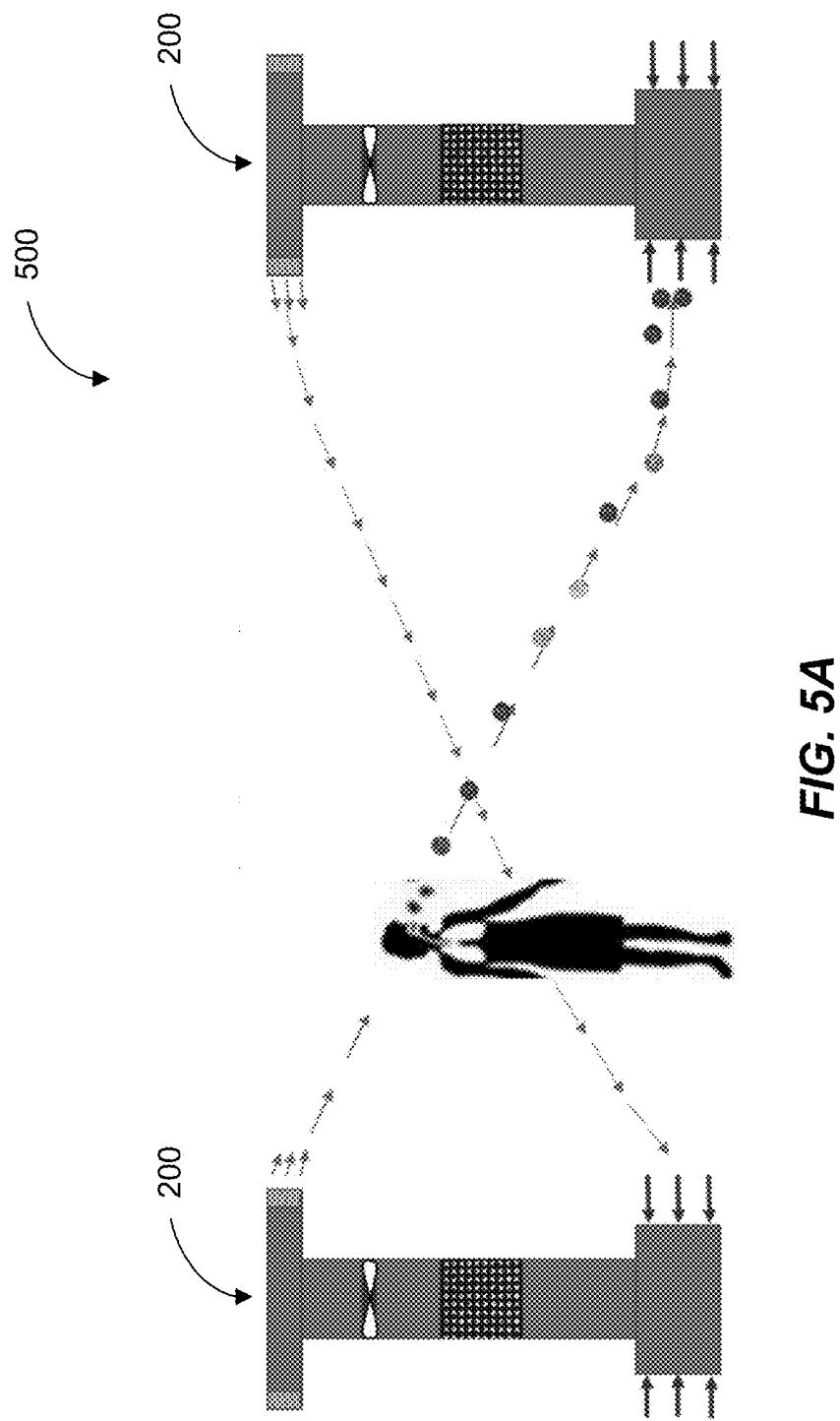
FIGS. 5A-5C illustrate example air sanitation systems, in accordance with the disclosed technology.
Figure 5B:
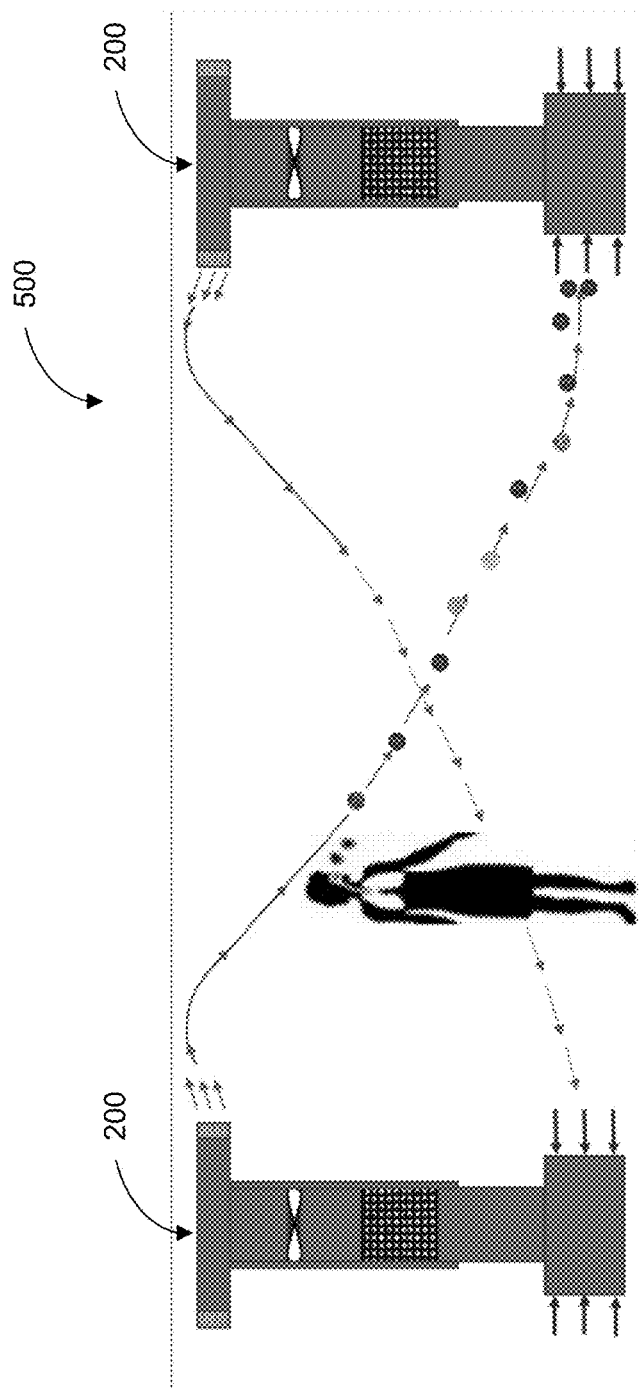
Figure 5C:
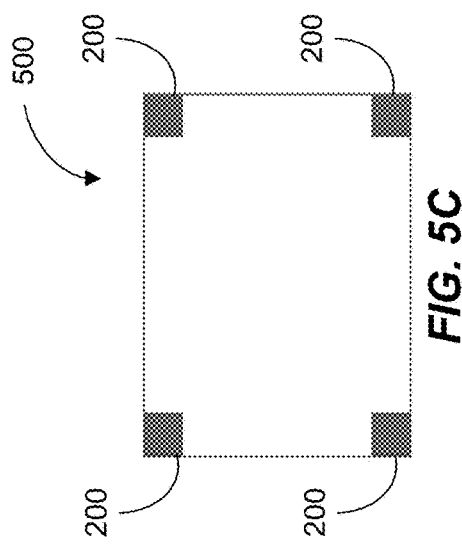

Referring to FIGS. 5A-5C, the disclosed technology includes an air sanitation system 500 that can include multiple air sanitation devices 200. As shown in FIG. 5A, the air sanitation devices 200 can be configured to direct air downwardly and toward the inlet of another air sanitation device 200. As another example and referring to FIG. 5B, the air sanitation devices 200 can be configured to direct air upwardly to rebound off the ceiling of the room in which the air sanitation device 200 is located, thereby directing the cleaned air toward the inlet of another air sanitation device 200. As yet another example, the air sanitation system 500 can include any combination of the disclosed air sanitation devices 200. Regardless, of the types of air sanitation devices 200 used, the air sanitation system 500 can reduce the amount and/or concentration of pathogens in the breathing zone within the room or conditioned space. Each air sanitation device 200 can be strategically positioned such that the outputted air is directed toward the inlet of another air sanitation device 200. Alternatively or additionally, one or more of the air sanitation devices 200 can include one or more sensors configured to detect the presence and location of other air sanitation devices. For example, a given air sanitation device 200 can be configured to detect a beacon signal broadcasted from another air sanitation device 200 (e.g., via Bluetooth, Bluetooth Low Energy). As another example, the air sanitation device 200 can include a flow sensor configured to detect the airflow outputted by another air sanitation device 200. As yet another example, the air sanitation device 200 can be configured to detect another air sanitation device 200 using a camera and visual recognition methods, a LiDAR system/sensor, an infrared system/sensor, an ultrasonic system/sensor, or the like. Alternatively or additionally, the air sanitation devices 200 can be configured to communicate with one another. The air sanitation devices 200 can be configured to move positions within the room or space (e.g., via the motorized wheel(s)) and/or adjust their corresponding heights and/or corresponding angles of outputted air flow to create efficient movement of air from the outlet of a given air sanitation device 200 to the inlet of another air sanitation device 200. As shown in FIG. 5C, the strategic positioning of air sanitation devices 200 can correspond to the corners of a room, although the strategic positioning depends on the size and geometry of the room. Although FIGS. 5A and 5B depict the air sanitation system 500 as including multiple air sanitation devices 200, it is contemplated that the air sanitation system 500 can include any number and combination of the disclosed air sanitation devices 200, 400.

As mentioned above, various scenarios have been tested with CFD simulations. FIGS. 6A and 6B illustrate the lateral travel of microdroplets relating to CFD simulations of persons sneezing in an indoor environment. In particular, FIG. 6A illustrates the lateral travel of microdroplets relating to a CFD simulation of persons sneezing in an indoor environment having an overhead HVAC configuration in which both the supply vents and the return vents are located overhead, and FIG. 6B illustrates the lateral travel of microdroplets relating to a CFD simulation of persons sneezing from the same locations within the same indoor environment with the same HVAC configuration, as well as air sanitation devices as disclosed herein. In FIGS. 6A and 6B, the dashed circles surrounding each person represents a six foot radius, which the prevailing social distancing guideline. As can be seen in FIG. 6A, microdroplets from the persons' sneezes travel well outside of the six foot radius. In contrast, sneezes occurring in the same room having implementations of the disclosed technology travelled a much shorter distance. Referring to FIG. 6B, the microdroplets from sneezes in the room with the air sanitation devices were almost entirely limited to the six foot radiuses.

Figure 7A:
FIGS. 7A and 7B illustrate comparative CFD simulations relating to an indoor environment with and without the disclosed technology, with FIG. 7A illustrating a CFD simulation of the indoor environment without the disclosed technology and FIG. 7B illustrating a CFD simulation of the indoor environment with the disclosed technology.
Figure 7B:
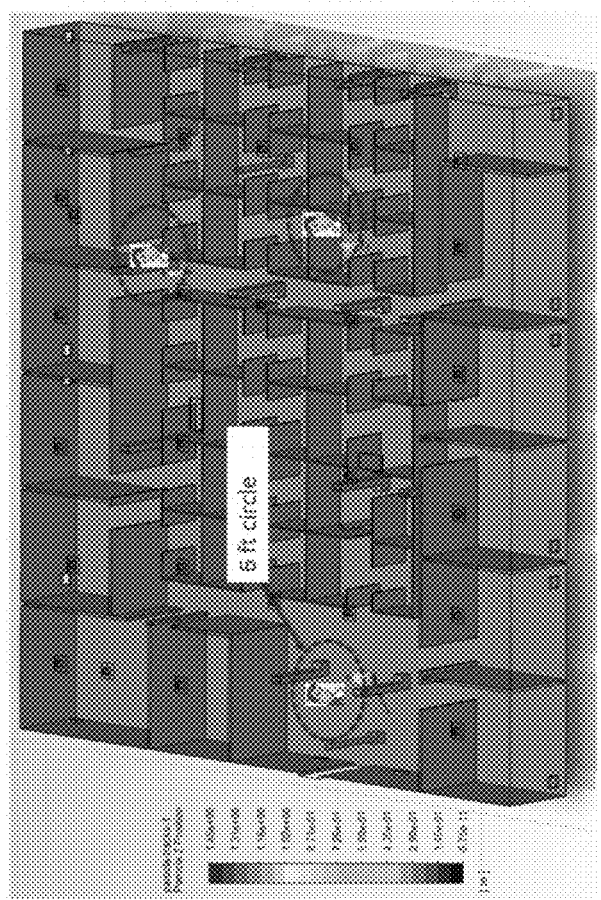

FIGS. 7A and 7D correspond to FIGS. 6A and 6B, respectively, but instead illustrate the vertical travel of microdroplets relating to CFD simulations of persons sneezing in an indoor environment. That is, FIG. 7A illustrates the vertical travel of microdroplets relating to a CFD simulation of persons sneezing in an indoor environment having an overhead HVAC configuration in which both the supply vents and the return vents are located overhead, and FIG. 7B illustrates the vertical travel of microdroplets relating to a CFD simulation of persons sneezing from the same locations within the same indoor environment with the same HVAC configuration, as well as air sanitation devices as disclosed herein. As can be seen in FIG. 7A, microdroplets from the persons' sneezes travel upwardly to heights in and above the breathing zone, which can help spread those microdroplets to other persons. In contrast, sneezes occurring in the same room having implementations of the disclosed technology tend to travel downwardly only. Referring to FIG. 7B, all or nearly all of the microdroplets from sneezes in the room with the air sanitation devices travel toward the ground at a rapid rate. Thus, as can be seen from the CFD simulations, the disclosed technology can greatly reduce the prevalence of pathogen-carrying microdroplets and aerosols in the breathing zone, which can reduce the likelihood of disease transmission.

Figure 8:
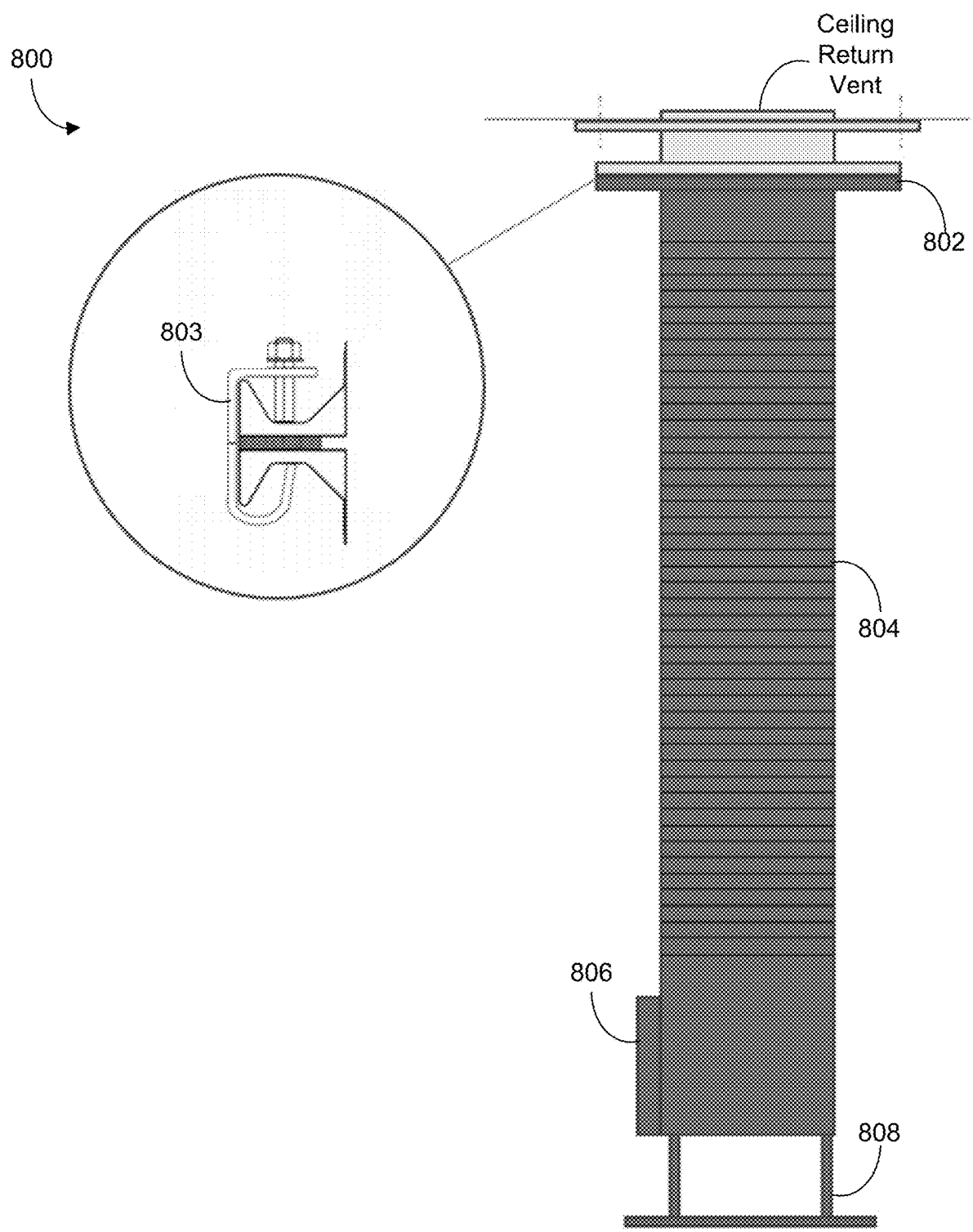
FIG. 8 illustrates a retrofit floor vent system, in accordance with the disclosed technology.

Moreover, as explained herein, the existing HVAC configuration of an indoor space can be detrimental to the facilitation of downward air flow of clean air. For example, HVAC systems having an overhead ventilation configuration (both the supply vents and the return vents are located overhead) can promote high circulation of microdroplets and/or pathogens throughout the space and the breathing zone of the space. Referring to FIG. 8, this can be combatted at least in part with a retrofit floor vent system 800. The retrofit floor vent system 800 can include an adapter 802 configured to attach to the existing ceiling return vent and/or the existing return duct, a duct 804, and a vent 806. The adapter 802 can be attached (e.g., permanently attached, detachably attached) to the exiting ceiling vent use any useful attachment method or device 803, such as by welding, brazing, or soldering, or using screws, bolts, nuts, one or more clamps, one or more adhesives, tape, and the like. As illustrated in FIG. 8, the adapter 802 can be detachably attached to the vent using one or more clamps, such as a G-clamp (although the use of other clamps is contemplated). The duct 804 can have an adjustable length such that the vent 806 can be positioned below the breathing zone (e.g., below approximately 4.5 feet) or at or near floor level. Of course, the duct 804 can be adjusted such that the vent 806 can be positioned at any desirable height with respect to the floor. Optionally, the duct can include a base 808, which can help position the vent 806 at a desired height above the floor.

In addition, the disclosed technology includes an air sanitation/circulation system 900, that can include one or more retrofit floor vent systems 800, one or more air sanitation devices 200, and/or one or more air sanitation devices 400. As will be appreciated, the number and respective positioning of the retrofit floor vent system(s) 800 and the air sanitation device(s) 200, 400 can be dependent on a particular room or indoor space. Regardless, the air sanitation/circulation system 900 can include any number of retrofit floor vent system(s) 800 and air sanitation device(s) 200, 400 as needed to effectively circulate clean air through the corresponding indoor space and, in particular, through the corresponding breathing zone of the indoor space.

To ensure the air sanitation/circulation system 900 is providing the maximum benefit, it can be useful to balance the air in all supply vents and/or diffusers to ensure there is an approximately equal flow rate of air within the indoor space. Alternatively or additionally, it can be advantageous to outfit the HVAC system (e.g., one or more supply units of the HVAC system) with one or more UV (e.g., UV-C) light arrays (e.g., similar to the UV light sources 224 described herein) and/or filters, which can help ensure air being discharged into the indoor space is clean. Combining some or all of these measures with a system of some or all of the disclosed retrofit floor vent system 800 and air sanitation devices 200, 400 can provide.

Figure 9A:
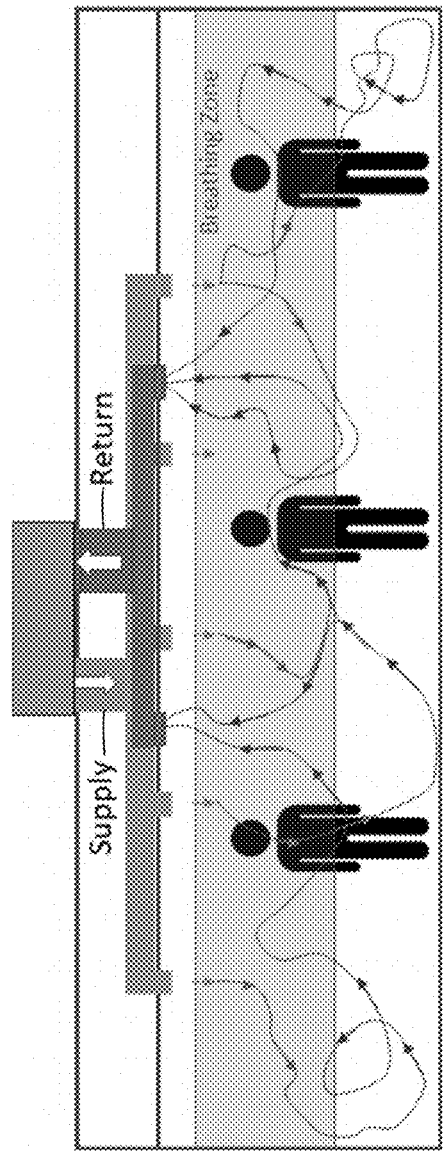
FIGS. 9A-9D illustrate example models showing the differences in the flow path of air in different indoor space both with and without the disclosed technology.
Figure 9B:
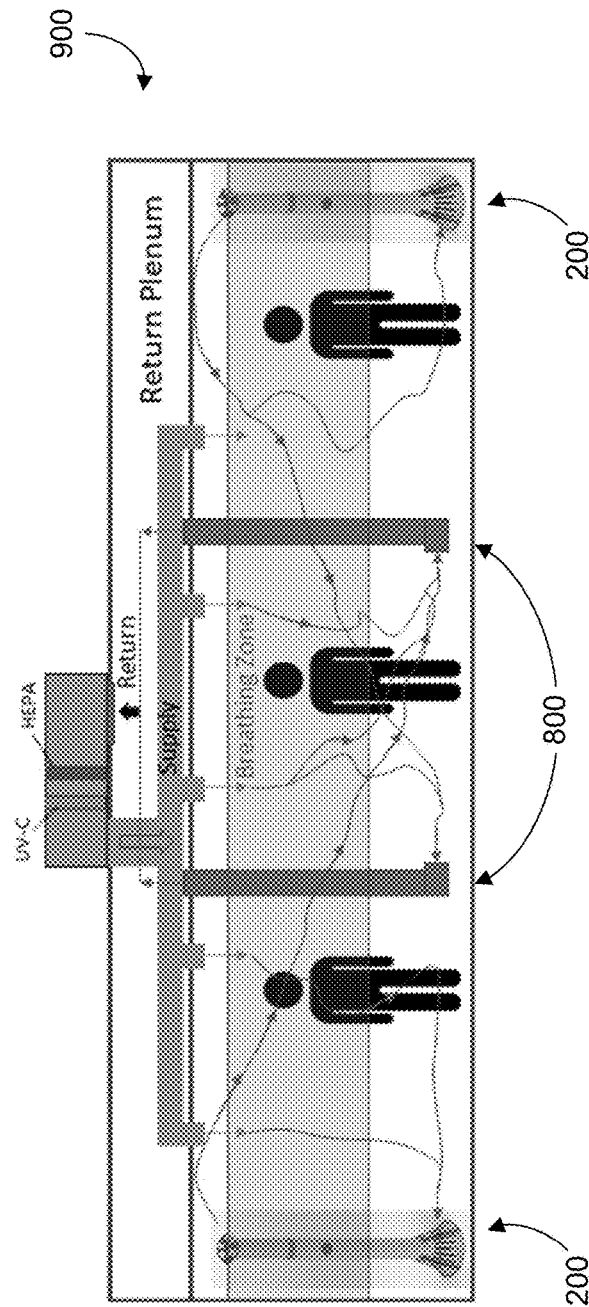

Referring to FIGS. 9A and 9B, example models illustrate the difference in the flow path of air in an open indoor space with and without the disclosed technology. In particular, FIG. 9A illustrates the general flow paths of air within an open indoor space lacking the disclosed technology. As can be seen, the air flow can be unpredictable and can generally swirl throughout the indoor space and throughout the breathing zone. In contrast, FIG. 9B illustrates the general flow paths of air within an open indoor space outfitted with an air sanitation/circulation system 900. In particular, FIG. 9B illustrates an air sanitation/circulation system 900 including multiple air sanitation devices 200 and multiple retrofit floor vent systems 800. As can be seen, the air flow within the open indoor space outfitted with an air sanitation/circulation system 900 is generally downward but, regardless, is quickly pushed or drawn out of the breathing zone within the indoor space.

Figure 9C:
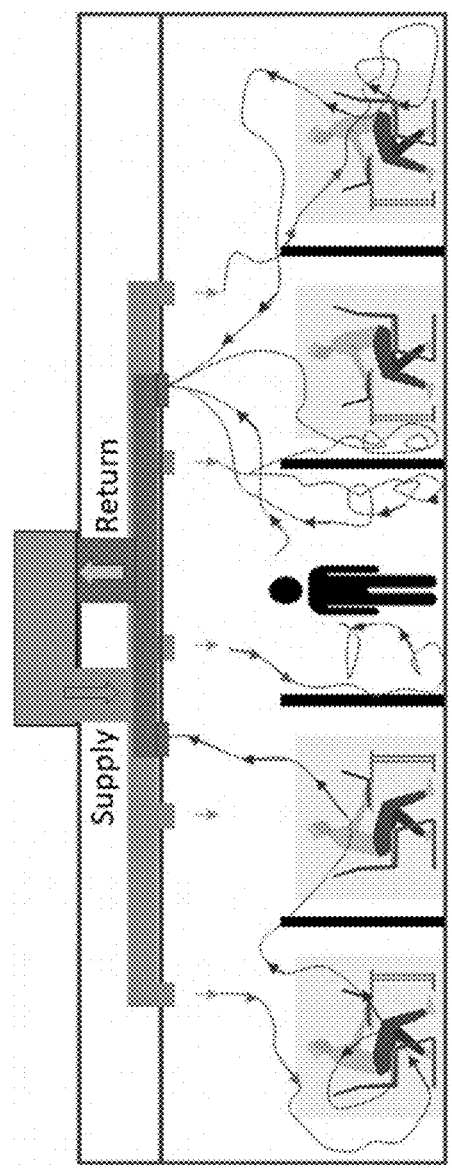
Figure 9D:
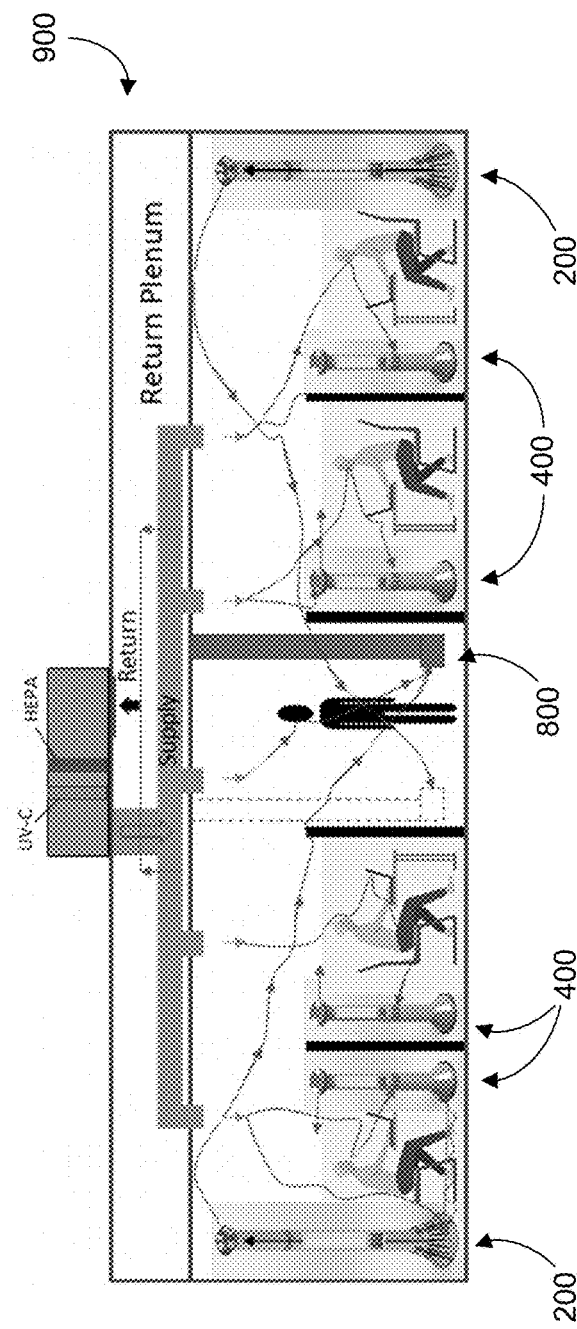

Similarly, FIGS. 9C and 9D provide example models illustrating the difference in the flow path of air in an indoor space having several barriers (e.g., cubicles). As can be seen in FIG. 9C, when the room when it is not outfitted with the disclosed technology, the air flow can be unpredictable and can generally swirl throughout the indoor space and throughout the breathing zone. As shown in FIG. 9D, however, an air sanitation/circulation system 900, in which various retrofit floor vent system(s) 800 and/or air sanitation device(s) 200, 400 are strategically positioned, can provide a flow of air that is generally downward but, regardless, is quickly pushed or drawn out of the breathing zone within the indoor space. Accordingly, the air sanitation/circulation system 900 can help prevent the spread of pathogens within the indoor space and particularly within the breathing zone.

In this description, numerous specific details have been set forth. It is to be understood, however, that implementations of the disclosed technology may be practiced without these specific details. In other instances, well-known methods, structures, and techniques have not been shown in detail in order not to obscure an understanding of this description. References to "one embodiment," "an embodiment," "one example," "an example," "some examples," "example embodiment," "various examples," "one implementation,"

"an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Further, certain methods and processes are described herein. It is contemplated that the disclosed methods and processes can include, but do not necessarily include, all steps discussed herein. That is, methods and processes in accordance with the disclosed technology can include some of the disclosed while omitting others. Moreover, methods and processes in accordance with the disclosed technology can include other steps not expressly described herein.

Throughout the specification and the claims, the following terms take at least the meanings explicitly associated herein, unless otherwise indicated. The term "or" is intended to mean an inclusive "or." Further, the terms "a," "an," and "the" are intended to mean one or more unless specified otherwise or clear from the context to be directed to a singular form. By "comprising," "containing," or "including" it is meant that at least the named element, or method step is present in article or method, but does not exclude the presence of other elements or method steps, even if the other such elements or method steps have the same function as what is named.

As used herein, unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An air sanitation device having a central axis extending therethrough in a generally vertical direction, the air sanitation device comprising:
a free-standing base section comprising one or more inlets disposed at a height that is less than or equal to approximately 4.5 feet with respect to a bottom of the base section;
a body section comprising one or more outlets disposed at a height that is greater than or equal to approximately 7 feet with respect to the bottom of the base section, each of the one or more outlets configured to discharge air in a plurality of discharge directions, each of the plurality of discharge directions being at least partially radially outward from the central axis;
an ultraviolet (UV) light source disposed in an interior of the air sanitation device;
an air movement device configured to move air into the base section via the one or more inlets, past the UV light source, and out of the body section via the one or more outlets; and
a controller configured to:
determine a location of an additional air sanitation device; and
output instructions for directing a flow of discharged air toward one or more inlets of the additional air sanitation device.

2. The air sanitation device of claim 1 further comprising a filter at least partially disposed in the interior of the air sanitation device.

3. The air sanitation device of claim 1, wherein the one or more outlets comprise an air distribution device configured to direct a flow such that at least some of the plurality of discharge directions has a downward angle.

4. The air sanitation device of claim 3, wherein the downward angle is between approximately 1 degree and approximately 30 degrees with respect to horizontal.

5. The air sanitation device of claim 1, wherein the one or more outlets comprise an air distribution device configured to direct a flow such that at least some of the plurality of discharge directions has an upward angle.

6. The air sanitation device of claim 5, wherein the upward angle is between approximately 1 degree and approximately 80 degrees with respect to horizontal.

7. The air sanitation device of claim 1, wherein at least some of the plurality of discharge directions are each in a generally horizontal direction.

8. The air sanitation device of claim 1, wherein the air movement device is configured to discharge air between approximately 150 cubic feet per minute (CFM) and approximately 200 CFM.

9. An air sanitation device having a central axis extending therethrough in a generally vertical direction, the air sanitation device comprising:
a free-standing base section comprising one or more inlets configured to draw in air at a height that is within a breathing zone defined as being between approximately 4.5 feet above ground and approximately 7.2 feet above ground;
a body section comprising one or more outlets configured to discharge air at a height that is greater than or equal to approximately 7 feet above ground, each of the one or more outlets configured to discharge air in a plurality of discharge directions, each of the plurality of discharge directions being at least partially radially outward from the central axis;
an ultraviolet (UV) light source disposed in an interior of the air sanitation device;
an air movement device configured to move air into the base section via the one or more inlets, past the UV light source, and out of the body section via the one or more outlets and
a controller configured to:
determine a location of an additional air sanitation device; and output instructions for directing a flow of discharged air toward one or more inlets of the additional air sanitation device.

10. The air sanitation device of claim 9, wherein the air sanitation device is configured to be installed on the ground, the one or more inlets being disposed at a height that is between approximately 4.5 feet and approximately 7.2 feet from a bottom of the base section.

11. The air sanitation device of claim 10, wherein the one or more inlets comprise at least one of (i) a first inlet disposed at a height that is approximately five feet with respect to the bottom of the base section and (ii) a second inlet disposed at a height that is approximately 7 feet with respect to the bottom of the base section.

12. The air sanitation device of claim 9, wherein the air sanitation device is configured to be installed on an elevated surface, the one or more inlets being disposed at a height that is between approximately 1.5 feet and approximately 2.5 feet from a bottom of the base section.

13. The air sanitation device of claim 12, wherein the one or more outlets are disposed at a height greater than approximately 2.75 feet from the bottom of the base section.

14. The air sanitation device of claim 9 further comprising a filter at least partially disposed in the interior of the air sanitation device.

15. The air sanitation device of claim 9, wherein at least some of the plurality of discharge directions are each in a generally horizontal direction.

16. The air sanitation device of claim 9, wherein the air movement device is configured to discharge an airflow between approximately 150 cubic feet per minute (CFM) and approximately 200 CFM.

17. An air sanitation system comprising:
a plurality of air sanitation devices comprising:
one or more first air sanitation devices, each of the one or more first air sanitation devices having a central axis extending therethrough in a generally vertical direction and comprising:
a free-standing base section comprising one or more inlets disposed at a height that is less than or equal to approximately 4.5 feet with respect to a bottom of the base section;
a body section comprising one or more outlets disposed at a height that is greater than or equal to approximately 7 feet with respect to the bottom of the base section, each of the one or more outlets configured to discharge air in a plurality of discharge directions, each of the plurality of discharge directions being at least partially radially outward from the central axis;
an ultraviolet (UV) light source; and
an air movement device configured to move air into the base section via the one or more inlets, past the UV light source, and out of the body section via the one or more outlets; and
one or more second air sanitation devices, each of the one or more second air sanitation devices having a central axis extending therethrough in a generally vertical direction and comprising:
a free-standing base section comprising one or more inlets disposed at a height that is within a breathing zone defined as being between approximately 4.5 feet above ground and approximately 7.2 feet above ground;
a body section comprising one or more outlets disposed at a height that is greater than or equal to approximately 7 feet with respect to the bottom of the base section, each of the one or more outlets configured to discharge air in a plurality of discharge directions, each of the plurality of discharge directions being at least partially radially outward from the central axis;
a UV light source; and
an air movement device configured to move air into the base section via the one or more inlets, past the UV light source, and out of the body section via the one or more outlets,
wherein at least one of the plurality of air sanitation devices is configured to:
determine a location of another of the plurality of air sanitation devices; and
output instructions for directing a flow of discharged air toward the one or more inlets of the another of the plurality of air sanitation devices.

18. The air sanitation system of claim 17 further comprising:
one or more floor vent adapters, each of the one or more floor vent adapters comprising:
an attachment adapter configured to attach to a ceiling return vent and/or a ceiling return duct;
a substantially vertically extending duct; and
an air intake vent configured to draw in air from a height less than approximately 4.5 feet with respect to ground.

19. The air sanitation system of claim 17, wherein determining the location of another of the plurality of air sanitation devices comprises at least one of:
receiving a signal from the another of the plurality of air sanitation devices;
receiving, from a sensor of the respective at least one of the plurality of air sanitation devices, sensor data indicative of a location of the another of the plurality of air sanitation devices; and
receiving, from a flow sensor of the respective at least one of the plurality of air sanitation devices, flow sensor data indicative of a detected airflow.

* * * * *